US009314486B2

(12) United States Patent
Guha et al.

(10) Patent No.: US 9,314,486 B2
(45) Date of Patent: Apr. 19, 2016

(54) PREPARATIVE REGIMEN FOR ENGRAFTMENT, GROWTH AND DIFFERENTIATION OF NON-HEMATOPOEITIC CELLS IN VIVO AFTER TRANSPLANTATION

(71) Applicants: Varian Medical Systems, Inc., Palo Alto, CA (US); Montefiore Medical Center, Bronx, NY (US)

(72) Inventors: Chandan Guha, Scarsdale, NY (US); Robert M. Sutherland, Menlo Park, CA (US); Alan Alfieri, Garden City, NY (US); Jayanta Roy-Chowdury, New Rochelle, NY (US)

(73) Assignees: Varian Medical Systems, Inc., Palo Alto, CA (US); Montefiore Medical Center, Bronx, NY (US)

( * ) Notice: Subject to any disclaimer, the term of this patent is extended or adjusted under 35 U.S.C. 154(b) by 158 days.

(21) Appl. No.: 13/625,649

(22) Filed: Sep. 24, 2012

(65) Prior Publication Data
US 2013/0149280 A1 Jun. 13, 2013

Related U.S. Application Data

(63) Continuation of application No. 12/032,615, filed on Feb. 15, 2008, now abandoned.

(60) Provisional application No. 60/890,444, filed on Feb. 16, 2007.

(51) Int. Cl.
*A61K 35/407* (2015.01)
*A61K 38/20* (2006.01)
*A61K 39/395* (2006.01)
*A61K 45/06* (2006.01)
*A61K 38/18* (2006.01)

(52) U.S. Cl.
CPC ........... *A61K 35/407* (2013.01); *A61K 38/1833* (2013.01); *A61K 38/204* (2013.01); *A61K 39/395* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 6,093,531 A | 7/2000 | Bjornson et al. | |
| 6,214,334 B1 | 4/2001 | Lee et al. | |
| 6,251,383 B1 | 6/2001 | Upadhyay et al. | |
| 2003/0054035 A1* | 3/2003 | Chu et al. | 424/486 |
| 2005/0005312 A1 | 1/2005 | Wu et al. | |
| 2005/0169896 A1* | 8/2005 | Li et al. | 424/93.7 |
| 2005/0244959 A1 | 11/2005 | Corlu et al. | |

OTHER PUBLICATIONS

Fine et al, Cacner, 1993, vol. 71, pp. 2585-2597.*
Down et al, Blood, 1991, vol. 77, No. 3, pp. 661-669.*
Nussembaum et al, The Laryngyoscope, 2005; vol. 115; pp. 1170-1177.*
Tacrine AHFS Consumer Medication Information (no author). U.S. National Library of Medicine: PubMed Health. Updated Sep. 1, 2008. Retrieved from URL: http://www.ncbi.nlm.nih.gov/pubmedhealth/pMH0000930/ on Nov. 8, 2011.
Berry et al., "High-Yeild Preparation of Isolated Rat Liver Parenchymal Cells," J Cell Biol, 1996, vol. 43, pp. 506-520.
Deb, N. et al., "Selective Hepatic Lobar Repopulation by Transplanted Hepatocytes After Ligation of a Portal Vein Branch and Preparative Hepatic Irradiation," *Hepatology*, Oct. 2001, vol. 34, No. 4, Pt. 2 of 2, Abstract No. 305, p. 250A.
Fox, I.J. et al., "Conditional Immortalization of Gunn Rat Hepatocytes: An *Ex Vivo* Model for Evaluation Methods for Bilirubin-UDP-Glucuronosyltransferease Gene Transfer," *Hepatology*, Mar. 1995, vol. 21, No. 3, pp. 837-846.
Guha, C. et al., "Amelioration of Radiation-induced Liver Damage in Partially Hepatectomized Rats by Hepatocyte Transplantation," *Cancer Research*, Dec. 1, 1999, vol. 59, pp. 5871-5874.
Guha, C. et al., "Amplification of Engrafted Hepatocytes by Preparative Manipulation of the Host Liver," *Artificial Organs*, 2001, vol. 25, No. 7, pp. 522-528.
Guha, C. et al., "Feasibility of Hepatocyte Transplantation-Based Therapies for Primary Hyperoxalurias," *Am J Nephrol*, 2005, vol. 25, pp. 161-170.
Guha, C. et al., "Liver Irradiation: A Potential Preparative Regimen for Hepatocyte Transplantation," *Int. J. Radiation Oncology Biology Physics*, 2001, vol. 49, No. 2, pp. 451-457.
Guha, C. et al., "Normal Hepatocytes Correct Serum Bilirubin After Repopulation of Gunn Rat Liver Subjected to Irradiation/Partial Resection," *Hepatology*, Aug. 2002, vol. 36, No. 2, pp. 354-362.
Gupta, S. et al., "Integration of Transplanted Hepatocytes Into Host Liver Plates Demonstrated With Dipeptidyl Peptidase IV-Deficient Rats," *Proc. Natl. Acad. Sci. USA*, Jun. 1995, vol. 92, pp. 5860-5864.
Gupta, S. et al., "Transplanted Hepatocytes Proliferate Differently After $CCl_4$ Treatment and Hepatocyte Growth Factor Infusion," *Am J Physiol Gastrointest Liver Physiol*, 1999, vol. 276, pp. G629-G638.
International Search Report mailed on Jun. 27, 2008, for PCT Application No. PCT/US08/54169 filed on Feb. 15, 2008, 3 pages.
Jakubowski, A. et al., "TWEAK Induces Liver Progenitor Cell Proliferation," *The Journal of Clinical Investigation*, Sep. 2005, vol. 115, No. 9, pp. 2330-2340.

(Continued)

*Primary Examiner* — Allison Fox
(74) *Attorney, Agent, or Firm* — Kilpatrick Townsend & Stockton LLP

(57) ABSTRACT

Disclosed are methods of obtaining an expanded population of mammalian ex vivo cells for treating a mammalian subject by (a) administering to a subject an effective amount of an agent that confers a growth disadvantage to at least a subset of endogenous cells at the site of engraftment; (b) administering to the subject an effective amount of a mitogenic stimulus for the ex vivo cells; and (c) administering the ex vivo cells to the subject, wherein the ex vivo cells engraft at the site and proliferate to a greater extent than the subset of endogenous cells, to repopulate at least a portion of the engraftment site with the ex vivo cells. The repopulated cells can be harvested or left at the engraftment site. Methods of treating brain injury in a subject by engrafting ex vivo cells at the site of injury are also described.

4 Claims, 12 Drawing Sheets

(56) References Cited

OTHER PUBLICATIONS

Katayama, S. et al., "Size-Dependent in Vivo Growth Potential of adult Rat Hepatocytes," *American Journal of Pathology*, Jan. 2001, vol. 158, No. 1, pp. 97-105.

Kawashita, Y. et al., "Liver Repopulation: A New Concept of Hepatocyte Transplantation," *Surgery Today*, 2005, vol. 35, pp. 705-710.

Laconi, E. et al., "Long-Term, Near-Total Liver Replacement by Transplantation of Isolated Hepatocytes in Rats Treated With Retrorsine," *American Journal of Pathology*, Jul. 1998, vol. 153, No. 1, pp. 319-329.

Landis, C.S. et al., "Noninvasive Evaluation of Liver Repopulation by Transplanted Hepatocytes Using $^{31}$P MRS Imaging in Mice," *Hepatology*, Nov. 2006, vol. 44, No. 5, pp. 1250-1258.

Malhi, H. et al., "Cell Transplantation After Oxidative Hepatic Preconditioning With Radiation and Ischemia-Reperfusion Leads to Extensive Liver Repopulation," *PNAS*, Oct. 1, 2002, vol. 99, No. 20, pp. 13114-13119.

Miki, T. et al., "Stem Cell Characteristics of Amniotic Epithelial Cells," *Stem Cells*, 2005, vol. 23, pp. 1549-1559.

Mitchell, C. et al., "Liver Repopulation by Bcl-$x_L$ Transgenic Hepatocytes," *American Journal of Pathology*, Jan. 2002, vol. 160, No. 1, pp. 31-35.

Nakatani, T. et al., "Mechanism for Peroxisome Proliferator-Activated Receptor-α Activator-Induced Up-Regulation of UCP2 mRNA in Rodent Hepatocytes," *The Journal of Biological Chemistry*, Mar. 15, 2002, vol. 277, No. 11, pp. 9562-9569.

Nowak, G. et al., "Identification of Expandable Human Hepatic Progenitors Which Differentiate into Mature Hepatic cells in Vivo," *Gut*, 2005, vol. 54, pp. 972-979.

Overturf, K. et al., "Serial Transplantation Reveals the Stem-Cell-Like Regenerative Potential of Adult Mouse Hepatocytes," *American Journal of Pathology*, Nov. 1997, vol. 151, No. 5, pp. 1273-1280.

Parashar, B. et al., "A Preparative Regimen for Massive Repopulation of the Liver by Transplanted Hepatocytes Consisting of Hepatic Irradiation and Triiodothyronine (T3) Therapy: Amelioration of Jaundice in Gunn Rats," *Hepatology*, Oct. 2000, vol. 32, Abstract No. 173, p. 206A.

Tada, K. et al., "Long-Term Reduction of Serum Bilirubin Levels in Gunn Rats by Retroviral Gene Transfer In Vivo," *Liver Transplantation and Surgery*, Jan. 1998, vol. 4, No. 1, pp. 78-88.

Takahashi, M. et al., "A Novel Strategy for In Vivo Expansion of Transplanted Hepatocytes Using Preparative Hepatic Irradiation and Fast-induced Hepatocellular Apoptosis," *Gene Therapy*, 2003, vol. 10, pp. 304-313.

Thomas, E.D. et al., "Bone-Marrow Transplantation (First of Two Parts)," *The New England Journal of Medicine*, Apr. 17, 1975, vol. 292, No. 16, pp. 832-843.

Yin, Y. et al., "AFP$^+$, ESC-Derived Cells Engraft and Differentiate Into Hepatocytes in Vivo," *Stem Cells*, 2002, vol. 20, pp. 338-346.

Kawashita et al., "Hepatic repopulation with stably transduced conditionally immortalized hepatocytes in the Gunn rat", *Journal of Hepatology* vol. 49, pp. 99-106 (2008).

Yamanouchi et al., "Hepatic Irradiation Augments Engraftment of Donor Cells Following Hepatocyte Transplantation", *Hepatology*, vol. 49, No. 1, p. 258-267 (2009).

* cited by examiner

PREPARATIVE REGIMEN FOR ENGRAFTMENT, GROWTH AND DIFFERENTIATION OF NON-HEMATOPOEITIC CELLS IN VIVO AFTER TRANSPLANTATION

CROSS-REFERENCES TO RELATED APPLICATIONS

This application claims priority benefit of U.S. patent application Ser. No. 12/032,615, which was filed on Feb. 15, 2008, and U.S. Provisional Patent Application Ser. No. 60/890,444 which was filed on Feb. 16, 2007, which are incorporated herein by reference in their entirety for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

FIELD OF THE INVENTION

This invention relates to methods of cell transplantation therapy in which the subject is administered an effective amount of an agent that confers a growth disadvantage to at least a subset of endogenous cells at the site of engraftment.

BACKGROUND OF THE INVENTION

Orthotopic whole organ transplantation is expensive and invasive. Moreover, there is an acute shortage of donor organs. Accordingly, cell transplantation has been considered as a potential alternative to whole organ transplantation. Cell transplantation has been around for two decades but has not been clinically very useful because even when primary or stem cells can engraft in organs they often cannot selectively proliferate or repopulate the intended organ. Accordingly, cell transplantation without a preparative regimen of is ineffective because of poor engraftment of the transplanted cells in the host organ. Administration of growth factors alone cannot offer selective proliferative/growth advantage to the transplanted cells over the residual host cells and have not been used clinically.

There is a great clinical need for cell transplantation treatments which can restore an organ to health and provide for its biological functions. For instance, with respect to liver disease, more than 40,000 patients die of terminal liver diseases every year in the United States alone, and it is estimated that approximately 20 million suffer from liver diseases (Hagmann, M., Science, 287:1185, 1187 (2000)). For those with inherited metabolic liver diseases or terminal liver failure, orthotopic liver transplantation (OLT) is the only treatment option, but most die without OLT because of a critical shortage of donor livers. Out of 1.3 million patients who may benefit from OLT, only about 4000 patients receive it each year (Hagmann, M., Science, 287:1185, 1187 (2000)). In theory, many patients with primary or metastatic cancers in the liver could also be cured, or have their survival and/or the quality of life improved, by total hepatectomy with OLT. In practice, however, cancer patients are rarely considered for OLT because of the long waiting lists for donor liver.

In a clinical trial of hepatocyte transplantation (HT), 7.5 billion normal allogeneic hepatocytes (representing ~5% of the hepatocyte mass) were transplanted in a 10-year old girl with Crigler-Najjar syndrome type 1 (Fox, I. et al., N Engl J Med, 338:1422-1426 (1998)). Although the study demonstrated the long-term safety of HT, only partial correction of the metabolic disorder was achieved, because of the lack of proliferation of the engrafted donor hepatocytes. Similarly, a clinical trial of ex vivo hepatic gene therapy in patients with familial hypercholesterolemia failed to demonstrate convincing therapeutic effect (Raper, S. et al., Ann Surg, 223:116-126 (1996); Grossman, M. et al., Nat Med, 1:1148-1154 (1995)) because only a fraction of the transplanted cells engrafted and those that engrafted failed to proliferate in the host liver.

While it has been established that HT can be employed safely in humans, its applicability remains limited by:
(i) a critical shortage of donor hepatocytes,
(ii) the number of hepatocytes that can be transplanted safely, without causing portal hypertension,
(iii) the inability of the transplanted hepatocytes to proliferate in the host liver, and
(iv) lack of a noninvasive method to evaluate the repopulation of transplanted hepatocytes in the liver.

New strategies to provide a selective growth advantage to the engrafted cells over the host endogenous cells of the target organ are needed. These strategies can allow the diseased host cells to be replaced progressively with normal ones.

BRIEF SUMMARY OF THE INVENTION

In a first aspect, the invention provides a method of treating a mammalian subject with an organ or tissue having a reduced function by engrafting mammalian ex vivo cells which supplement the function of the organ or tissue and by promoting proliferation of the engrafted cells at the site of engraftment by (a) administering to the subject an effective amount of an agent that confers a growth disadvantage to at least a subset of endogenous cells at the site of engraftment, (b) administering to the subject an effective amount of a mitogenic stimulus or stimuli for the ex vivo cells, and (c) administering the ex vivo cells to the subject, wherein the ex vivo cells engraft at the site and proliferate to a greater extent than the subset of endogenous cells, thereby repopulating at least a portion of the engraftment site with the ex vivo cells, so that the repopulated ex vivo cells supplement the function. In some embodiments, the organ with the reduced function is intestine, brain, liver, lung, kidney, pancreas, eye, testes, ovary, or skin. In other embodiments, the organ or tissue with the reduced function was damaged by irradiation, trauma, chemical or drug exposure, a genetic illness, or an infectious disease. In additional embodiments, the ex vivo cells can be adult somatic cells, adult progenitor cells, adult stem cells, embryonic progenitor cells, fetal cells, and embryonic stem cells from the same species as the subject or from a different mammalian species than the subject. The ex vivo cells can be autologous or heterologous with respect to the subject. In yet other embodiments, the ex vivo cells are cultured prior to their administration to the subject. In still other embodiments, the ex vivo cells are harvested and sorted from a heterogeneous cell population prior to their administration to the subject. In some embodiments, the engrafted cells are of the same cell type as the cells of the organ or tissue at the site of engraftment.

In other embodiments, the agent that confers a growth disadvantage to at least a subset of endogenous cells is radiation (e.g. x-ray and gamma ray), a cytotoxic chemical, ultrasound, heat, biological agent, degenerative proteins, and proteins or nucleic acids that suppress cell division. The protein may be an antibody directed to a cell surface receptor that regulates cell division or apoptosis.

In other embodiments, the mitogenic stimulus may comprise one or more growth factors for the cell type to be engrafted. In some embodiments, the growth factors are one, two, three or more growth factors selected from the group consisting of HGF, EGF, FGF, VEGF, NGF, 11-6, TNF-alpha, CTNF, R-spondin 1, Noggin, and TWEAK. In other embodiments, the administered ex vivo cells comprise, contain, or include a heterologous gene that increases their intrinsic proliferation capacity or survival. In some embodiments, the mitogenic stimulus can comprise a biological agent, antibody or peptide factor that increases the proliferation capacity of the donor cells or comprise a procedure that deliberately injures the engraftment site to enable entry and integration of the transplanted cells into the host parenchyma and/or to provide a compensatory growth signal for the ex vivo cells. In some further embodiments, the procedure is a surgical resection, portal vein branch ligation, portal vein embolism by chemotherapeutic agents or toxins, radiofrequency ablation, radiosurgical ablation, or high frequency ultrasonic ablation of the a portion of the donor organ.

The subject to be treated is a mammal, preferably, a human. The ex vivo cells can be heterologous to the engraftment site. In some other embodiments, the engraftment site is the organ or tissue having the reduced function or elsewhere. In some embodiments, the ex vivo cells express a heterologous nucleic acid for gene therapy of the reduced function. In further embodiments of any of the above, immunosuppressive therapy is also administered to the host following administration of the ex vivo cells.

There is, in some further embodiments, a proviso that the organ or tissue is not bone marrow or a proviso that the damage is not due to cancer or a cancer. There is, in some further embodiments, a proviso that the damage to be treated is one which was not caused by exposure to the agent to be used to confer the growth disadvantage. There is, in some further embodiments, a proviso that the damaged organ or tissue is not the pancreas or islet cell. In some embodiments, there is a proviso that the mammalian growth factor is not HGF or a nucleic acid encoding HGF (e.g., an adenoviral vector comprising a nucleic acid encoding HGF).

In some embodiments, the ex vivo cell is derived from a precursor cell which is capable of differentiating into a cell type of the engraftment site or of the organ or tissue with the reduced function. In some embodiments, the ex vivo cell can be an epithelial cell, a hepatocyte, a nerve cell, a muscle cell, a kidney cell, a pancreatic islet β-cell or a precursor thereto. In some embodiments, the ex vivo cells are genetically modified to modulate or eliminate the expression of an endogenous gene or to express a gene encoding a protein not endogenous expressed in the cell. in some embodiments, the cells have been genetically modified to enhance their proliferation rate or survival without immortalization. In some further embodiments, the cells are genetically modified to become immortalized.

Where the ex vivo cells are sensitive to the growth disadvantaging properties of the agent that confers a growth disadvantage to at least a subset of the endogenous cells of the organ, step (a) is performed before step (c). Otherwise steps (a), (b) and (c) may be performed concurrently or in any order. With a preferred order having step (a) being performed first and then step (b) followed by step (c), or steps (b) and (c) being performed concurrently, or step (c) being performed before step (b). In instances, where the ex vivo cells are antigenically different from the host, immunosuppressive therapy may be further administered.

In some embodiments, the ex vivo cell expresses a protein not expressed by the host tissue at its engraftment site and the presence of the protein is used to selectively detect the ex vivo cells as opposed to the host cells at the engraftment site. In a further embodiment, the protein is an enzyme whose reaction products are detected using magnetic resonance spectroscopic imaging. In some further embodiments still, the protein is creatine kinase and a reaction product (e.g., phosphocreatine) containing $^{31}P$ is detected using magnetic resonance spectroscopic imaging in vivo.

In additional embodiments, the invention also provides a method of treating a subject with a damaged organ or tissue/organ or tissue having a reduced function by grafting ex vivo cells onto the organ or tissue and promoting proliferation of the engrafted cells by (a) administering to the subject an effective amount of an agent that confers a growth disadvantage to at least a subset of endogenous cells of the damaged organ; (b) administering to the subject an effective amount of a mitogenic stimulus for the ex vivo cells; and (c) administering the ex vivo cells to the organ, wherein the ex vivo cells engraft and proliferate and the endogenous cells having a growth disadvantage fail to proliferate or proliferate at a reduced rate or lesser rate than the engrafted ex vivo cells, thereby repopulating the damaged organ or tissue with ex vivo cells and treating the subject with the damaged organ or tissue. Where the ex vivo cells are sensitive to the growth disadvantaging properties of the agent that confers a growth disadvantage to at least a subset of the endogenous cells of the organ, step (a) is performed before step (c). Otherwise steps (a), (b) and (c) may be performed concurrently or in any order. With a preferred order having step (a) being performed first and then step (b) followed by step (c), or steps (b) and (c) being performed concurrently, or step (c) being performed before step (b). The damage can be due to trauma, surgery, or disease. The disease may be inherited/genetic or caused by an environmental agent (e.g., dietary deficiency, drug treatment, radiation, chemical exposure, or infectious agent). In some embodiments, the damaged organ is the liver, intestine, pancreas, heart, kidney, or a part of the central nervous system (e.g., brain, spinal cord). In other embodiments, the damage to be treated is not cancer and/or a result of a cancer. In yet other embodiments, the subject does not have cancer. The subject can be a mammal (e.g., human, a non-human primate (e.g., a chimpanzee, baboon), a rodent (e.g., a mouse, a rat) a pig, a rabbit). In instances, where the ex vivo cells are antigenically different from the host, immunosuppressive therapy may be further administered. In some embodiments, the methods is practiced in utero to treat a congenital disease. Accordingly, in some embodiments the organ or tissue to be engrafted in utero is a fetal organ or tissue or the organ whose function is to be supplemented in utero is a fetal organ or tissue.

In some embodiments, the ex vivo cells are adult somatic cells, adult progenitor cells, adult stem cells, embryonic progenitor cells, fetal cells, xenogenic cells, or embryonic stem cells. The ex vivo cells can be fetal hepatocytes, amniotic epithelial cells, "oval" cells and "small" hepatocytes. In still other embodiments, the ex vivo cells are heterologous to the subject. In still other embodiments, the ex vivo cells are autologous to the subject. In additional embodiments, the ex vivo cells are the same cell type as an endogenous cell type of the organ or tissue or heterologous to the organ or tissue. In other embodiments, the ex vivo cells are not an endogenous cell type of the organ or tissue. The ex vivo cells can be cultured prior to administration. In some embodiments, the ex vivo cells express a heterologous nucleic acid for gene therapy. In some embodiments, the grafted cells repopulate the damaged organ or tissue with healthy cells of the same type and/or function as those whose growth was targeted to be disadvantaged, or disadvantaged, by administration of the agent that confers a growth disadvantage. In some embodiments, the ex vivo cells are bone marrow progenitor cells, embryonic stem cells, neural progenitor cells, endothelial progenitor cells, progenitor cells obtained from peripheral blood, cord blood cells, amniotic epithelial cells, fetal cells, organ-specific stem cells, such as, oval cells, primary hepatocytes, primary parenchymal cells, human umbilical microvascular endothelial cells, blood outgrowth endothelial cells, glia, or human brain microvascular endothelial cells.

The agent that confers a growth disadvantage to at least a subset of endogenous cells of the damaged organ can be radiation (e.g., X-rays, gamma rays), cytotoxic chemicals (e.g., a compound which is hepatotoxic or toxic to liver parenchymal cells or more preferably selectively toxic for such; ultrasound; heat (e.g., focused ultrasound induced heating); biological agents; degenerative proteins; or proteins that suppress cell division. In some embodiments, the agent is partial liver irradiation (e.g., using 3-D conformal RT). For instance, hepatic irradiation can be delivered to portions of the liver while other portions are shielded (e.g., the right anterior lobes of the liver can be irradiated after shielding the left anterior and right posterior and caudate lobes using lead shields). The radiation in some embodiments is Stereotactic Radiosurgery (SRS), Intensity-Modulated Radiation Therapy (IMRT), dynamic adaptive radiation therapy, or image-guided radiation therapy (IGRT). Accordingly, in some embodiments, use of spatially confined, focally ablative regimen of single-fraction or hypofractionated irradiation for stem cell engraftment and growth of human primary parenchymal cells is contemplated.

The mitogenic composition can be a mammalian growth factor (e.g., hepatocyte growth factor (HGF), TGF-beta (transforming growth factor-beta), neurotrophins (NGF, BDNF, and NT3), Granulocyte-colony stimulating factor (G-CSF), Granulocyte-macrophage colony stimulating factor (GM-CSF), Platelet-derived growth factor (PDGF), Erythropoietin (EPO), Thrombopoietin (TPO), Myostatin (GDF-8), Growth Differentiation factor-9 (GDF9), basic fibroblast growth factor (bFGF or FGF2), epidermal growth factor (EGF), fibroblast growth factor (FGF), vascular endothelial growth factor (VEGF), nerve growth factor (NGF), interleukin-6 (11-6), tumor necrosis factor-alpha (TNF-alpha), circulating tumour necrosis factor (CTNF), R-spondin 1, Noggin, c-met activating antibody, and tumor necrosis factor-like weak inducer of apoptosis (TWEAK, growth receptor ligand) which can be selective for the type of transplated cell. The mitogen can be administered in the form of gene therapy or as a protein preparation. The protein may be recombinant. In some embodiments, the proliferative stimuli or mitogenic composition can be either a combination of growth factors such as HGF+ tri-iodo-thyronine (T3), or HGF+EGF, or a combination of growth factor and compensatory regenerative stimuli.

In some embodiments, the organ damage is a degenerative disease (e.g, a neurodegenerative disease). In other embodiments, the organ damage is a disease selected from the group consisting of liver cancer, hepatitis A, hepatitis B, hepatitis C, hepatic fibrosis, cirrhosis, Wilson's disease, alpha1-antitrypsin disease, Niemann-Pick disease, Tyrosinemia Type I, Protophophyria, Ornithine transcarbamylase deficiency, Parkinson's disease, Alzheimer's disease, and Crohn's disease; hepatitis, inflammation of the liver, caused mainly by various viruses but also by some poisons and/or chemicals (e.g., carbon tetrachloride), autoimmunity or hereditary conditions. hemochromatosis; primary sclerosing cholangitis; primary biliary cirrhosis, autoimmune disease of small bile ducts; Budd-Chiari syndrome, obstruction of the hepatic vein; and Gilbert's syndrome, a genetic disorder of bilirubin metabolism; biliary atresia, alpha-1 antitrypsin deficiency, alagille syndrome, and progressive familial intrahepatic cholestasis. In some embodiments, the organ with the reduced function is the kidney, liver, brain, heart, eye, testes, ovary, skin, lung, pancreas, spleen, or kidney. In some embodiments, the ex vivo cell is derived from a precursor cell which is capable of differentiating into a cell type of the engraftment site or organ with the reduced function. In some embodiments, the ex vivo cell can be an epithelial cell, a hepatocytes, a nerve cell, a muscle cell, a pancreatic islet β-cell or a precursor thereto.

Accordingly, the invention provides a method of treating a subject having organ damage due to radiation exposure, infection, or toxic exposure, the method comprising the steps of administering to the subject an effective amount of a mitogenic composition; and administering ex vivo cells to the subject, wherein the ex vivo cells engraft and proliferate, thereby repopulating the damaged organ. In some embodiments, the grafted cells can serve to repopulate the damaged organ with healthy cells of the same type and/or function as those damaged by the radiation exposure, infection or toxic exposure. In some embodiments, the damaged organ is the liver, intestine, pancreas, heart, kidney, lungs, brain, spleen eye, testes, ovary, or spinal cord, or a part of the central nervous system (e.g., brain, spinal cord). In other embodiments, the damage to be treated is not cancer and/or a result of a cancer. In yet other embodiments, the subject does not have cancer. The subject can be a human, a non-human animal, a mammal (e.g., human, a non-human primate (e.g., a chimpanzee, baboon), a rodent (e.g., a mouse, a rat) a pig, a rabbit).

In some embodiments, the ex vivo cells are also adult somatic cells, adult progenitor cells, adult stem cells, embryonic progenitor cells, or embryonic stem cells. In still other embodiments, the ex vivo cells are heterologous to the subject. In still other embodiments, the ex vivo cells are autologous to the subject. In additional embodiments, the ex vivo cells are the same cell type as an endogenous cell type of the organ or heterologous to the organ. In other embodiments, the ex vivo cells are not an endogenous cell type of the organ. The ex vivo cells can be cultured prior to administration. In some embodiments, the ex vivo cells express a heterologous nucleic acid for gene therapy. The mitogenic composition in this aspect can be a mammalian growth factor (e.g., HGF, EGF, FGF, VEGF, NGF, 11-6, TNF-alpha, CTNF, R-spondin 1, Noggin, and TWEAK).

In some embodiments, the invention provides methods of treating an organ damaged by exposure to toxic chemicals. The toxic effects and target organs for a variety of chemicals are disclosed in Registry of Toxic Effects of Chemical Substances (RTECS), RTECS (NIOSH 1980 or later editions, including 1995). RTECS is a database of toxicity information compiled from the published scientific literature. Prior to 2001, RTECS was maintained by US National Institute for Occupational Safety and Health (NIOSH). Now it is maintained by Elsevier MDL. See, also, Olson et al. Ed., *Poisoning and Drug Overdose,* 5th Edition, published by McGraw Hill/Lange for a listing of toxic agents and their effects and target organs.

There is in some further embodiments, a proviso that the organ is not bone marrow or a proviso that the damage is not due to cancer or cancer.

In one embodiment, endothelial (progenitor, microvascular and/or differentiated) cell transplantation is used to rescue radiation-induced gastro-intestinal injury, especially after exposure to irradiation to the intestines or whole body.

In another embodiment, the invention provides a method of grafting ex vivo cells onto a liver or other organ and promoting proliferation of the engrafted cells in a subject by (a) administering to the subject an effective amount of an agent that confers growth disadvantage to at least a subset of endogenous cells of the liver or other organ; (b) administering to the subject an effective amount of a mitogenic composition; and (c) administering the ex vivo cells to the subject, wherein the ex vivo cells engraft and proliferate and the endogenous cells having a growth disadvantage proliferate to a lesser extent, thereby repopulating the liver or other organ with the ex vivo cells. Where the ex vivo cells are sensitive the growth disadvantaging properties of the agent that confers a growth disadvantage to at least a subset of the endogenous cells of the organ, step (a) is performed before step (c). Otherwise steps (a), (b) and (c) may be performed concurrently or in any order. With a preferred order having step (a) being performed first and then step (b) followed by step (c), or steps (b) and (c) being performed concurrently, or step (c) being performed before step (b). In yet other embodiments, there is the further step, after steps (a) to (c), of transplanting the ex vivo cells into a human subject. In embodiments, the ex vivo cells are adult somatic cells, adult progenitor cells, adult stem cells, embryonic progenitor cells, or embryonic stem cells which can differentiate into a parenchymal cell of the host organ or (in the case of a heterotopic engraftment) of another organ whose functional activity is deficient in the host. In still other embodiments, the ex vivo cells are heterologous to the subject. In some embodiments, the ex vivo cells are human. In still other embodiments, the ex vivo cells are autologous, allogeneic, or xenogenic to the subject. In additional embodiments, the ex vivo cells are the same cell type as an endogenous cell type of the organ or heterologous to the organ. In other embodiments, the ex vivo cells are not an endogenous cell type of the organ and are cultured prior to administration. In some embodiments, the ex vivo cells express a heterologous nucleic acid for gene therapy. In other embodiments, the ex vivo cells have been genetically modified to eliminate a gene or to increase or decrease the expression of a protein. In still another embodiment, the ex vivo cell is an immortalized cell. In other embodiments of any of the above, the ex vivo cell is optionally further modified to contain genes whose expression is under the control of a promoter sensitive to a specific agent (drug, compound, heat, radiation) wherein the genes so controlled express a protein functioning as a maker or modulating cell function, cell growth, cell replication, apoptosis, or survival. The heterologous nucleic acid may express a protein needed by the subject. The organ may be damaged or healthy. In some embodiments of any of the above, the ex vivo cells are liver cells and the target organ is the liver. The subject can be a human or a mammal (e.g., a non-human primate (e.g., a chimpanzee, baboon, macaque), a rodent (e.g., a mouse, a rat) a pig, a rabbit). In instances, where the ex vivo cells are antigenically different from the host, immunosuppressive therapy may be further administered. In further embodiments of the above, the invention provides a preparative regimen of hepatic irradiation and hepatic mitotic signals, such as, hepatocyte growth factors to grow adult primary human hepatocytes or human stem cells in a non-human liver. Development of chimeric immunodeficient or tolerized immunocompetent (non-human mammals (e.g., mice, SCID mice, nude mice) with human liver cells or human stem cells is contemplated wherein such mice can be used as a source of human origin cells (e.g., stem and parenchymal cells) for ex vivo transplants in humans in need thereof.

The agent that confers a growth disadvantage to at least a subset of endogenous cells of the engraftment site or damaged organ can be ionizing radiation (e.g., X-rays, gamma rays, ARC therapy, TOMO therapy, particle therapy, electron therapy, proton therapy, carbon ion therapy). cytotoxic chemicals, ultrasound, heat, biological agents, degenerative proteins, or proteins that suppress cell division. The mitogenic composition can be a mammalian growth factor (e.g., HGF, EGF, FGF, VEGF, NGF, 11-6, TNF-alpha, CTNF, R-spondin 1, Noggin, and TWEAK). In some embodiments, the agent is partial liver irradiation (e.g., using 3-D conformal RT). For instance, hepatic irradiation can be delivered to portions of the liver while other portions are shielded (e.g., the right anterior lobes of the liver can be irradiated after shielding the left anterior and right posterior and caudate lobes using lead shields). The radiation in other embodiments is SRS, Intensity-Modulated Radiation Therapy (IMRT), dynamic adaptive radiation therapy, or image-guided radiation therapy (IGRT).

With respect to the liver, preparative hepatic irradiation can be used to facilitate stem cell/liver cell transplantation for i) the treatment of inherited liver diseases, ii) liver failure, iii) ex vivo hepatic gene therapy, iv) rescuing patients with liver cancer, following chemotherapy or radiation therapy, and v) expanding human hepatocytes in animal liver for generating animal models for human-specific hepatic infections and human hepatic responses to hepatoxic agents, metabolism of drugs, or the response of the human liver to therapeutic treatments in various disease states (e.g., infection (e.g., HCV, HBV), toxicity).

Accordingly, in some embodiments, the invention provides a method of obtaining an expanded population of ex vivo cells by (a) administering to a non-human mammalian subject an effective amount of an agent that confers a growth disadvantage to at least a subset of endogenous cells at a site of engraftment; (b) administering to the non-human mammalian subject an effective amount of a mitogenic stimuli for the ex vivo cells; and (c) administering the ex vivo cells to the subject, wherein the ex vivo cells engraft at the site and proliferate to a greater extent than the subset of endogenous cells, thereby repopulating at least a portion of the engraftment site with the ex vivo cells, and (d) harvesting the repopulated cells from the engraftment site; thereby obtaining the expanded ex vivo cell population. In some of these embodiments, the ex vivo cells are human. In other further embodiments, the ex vivo cells are selected from the group consisting of adult somatic cells, adult progenitor cells, adult stem cells, embryonic progenitor cells, fetal cells, xenogenic cells, and embryonic stem cells. In some embodiments, the ex vivo cells heterologous to the non-human subject. In yet other embodiments, the agent that confers a growth disadvantage to at least a subset of endogenous cells of the organ is radiation (e.g., x-ray and gamma ray). In still another further embodiment, the agent that confers a growth disadvantage to at least a subset of endogenous cells of the engraftment site is selected from the group consisting of cytotoxic chemicals, ultrasound, heat, biological agents, degenerative proteins, and proteins that suppress cell division. In additional further embodiments, the mitogenic stimulus comprises one or more (e.g., 1, 2, 3, or 4) growth factors selected from the group consisting of HGF, EGF, FGF, VEGF, NGF, 11-6, TNF-alpha, CTNF, R-spondin 1, Noggin, and TWEAK. In still additional further embodiments, the ex vivo cell is derived from brain, intestinal, or liver tissue.

In a further related aspect, the invention provides a method of treating a subject having a damaged organ or tissue or an organ or tissue with reduced function by engrafting cells obtained by the above methods. In some embodiments, the organ is intestine, liver, lung, kidney, pancreas, eye, testes, brain, ovary, or skin. In another aspect accordingly, the invention provides a chimeric non-human animal and methods of making such an animal as described above which has greater than 50, 60, 70 percent or near total replacement (e.g., 80, 85, 90, 95, 98 percent) of its host organ by engrafted ex vivo cells (e.g, a host liver repopulated with 50, 60, 70 percent, or near total replacement by, human primary hepatocytes or human organ specific stem cells).

In another aspect, the invention provides a method of treating a mammalian subject having a damaged central nervous system (e.g., brain, spinal cord) with a reduced function by engrafting mammalian ex vivo cells at the site of injury, by (a) administering to the subject an effective amount of an agent that increases the engraftment of ex vivo cells at the site of injury; (b) optionally administering to the subject an effective amount of a mitogenic stimuli for the ex vivo cells; and (c) administering the ex vivo cells to the subject, wherein the ex vivo cells engraft at the site of injury and repopulate at least a portion of the site with the ex vivo cells, wherein the repopulated ex vivo cells supplement the function, thereby treating the subject. In this aspect, the ex vivo cells can be selected from the group consisting of adult somatic cells, adult neuron progenitor cells, adult stem cells, embryonic progenitor cells, fetal cells, xenogenic cells, and embryonic stem cells which are capable of populating the site of injury with neurons.

In another aspect, the invention provides methods for the isolation and/or purification of HPCs from donor livers by selecting cells therefrom for the presence of the EpCAM marker. Accordingly, in some embodiments, above aspects and embodiments of the invention employ HPCs which have been selected for or sorted according to the presence of the EpCAM marker.

ABBREVIATIONS

ALT, Alanine transaminase
AST, Aspartate transaminase
ATP, Adenosine tri-phosphate
BrdU, bromodeoxyuridine
CRT, conformal radiation therapy
DCF, 2',7'-dichlorofluorescin diacetate
DPPIV, Dipeptidyl peptidase IV
F344, Fischer 344 rats
GGT, γ-glutamyl transpeptidase
HGF, Hepatocyte Growth factor
HIR, Hepatic irradiation
HT, Hepatocyte transplantation
IR, ionizing radiation
LDH, Lactose dehydrogenase
OLT, Orthotopic Liver Transplantation
PET, Positron emission tomography
PH, Partial hepatectomy
PVBL, Portal vein branch ligation
RILD, radiation-induced liver disease
RT, Radiation therapy
SRS, Stereotactic radiosurgery
T3, tri-iodo-thyronine
UGT1A1, bilirubin-UDP-glucuronosyltransferase
VOD, veno-occlusive disease

DETAILED DESCRIPTION OF THE INVENTION

Figure 1:
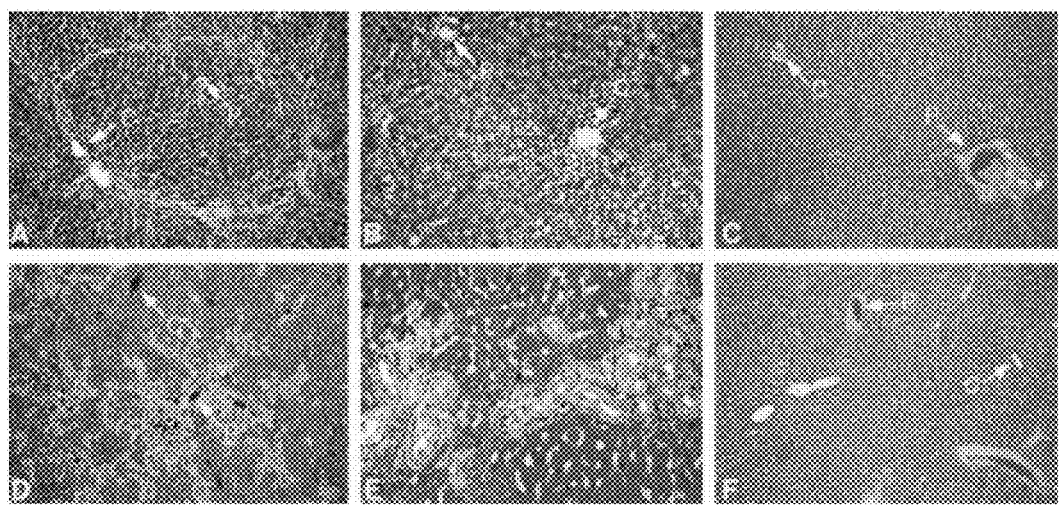
FIG. 1. HT ameliorates histomorphological changes of RILD. A, hepatocellular loss around central veins (C) in rats receiving PH+HIR at 2 weeks. B, centrizonal steatosis in PH+HIR rats at 1 week. C, amelioration of perivenous hepatocellular loss and steatosis after 1 week of HT. D and E, Extensive proliferation of oval cells and bile duct proliferation extending from portal tract (P) in PH+HIR rats at 17 weeks. F, amelioration of bile duct proliferation and fibrosis in transplanted rat at 17 weeks.

Our experiments demonstrate that parenchymal cell transplantation is of benefit in ameliorating radiation injury and other injury to organs. FIG. 1 D-E demonstrates parenchymal cell transplantation can modulate the late effects of RT. Accordingly, cell transplantation can replace the loss of parenchymal cells due to radiation or other injury of organs. In our RILD model of PH+HIR in rats, we observed that adult liver stem cells (a.k.a oval cells) proliferate extensively and attempt to restore the parenchymal cell loss caused by PH and HIR. Therefore, it was contemplated that adult progenitor cells or stem cells can engraft in injured organs, such as, liver and can differentiate into organ-specific parenchymal cells. Thus a preparative regimen of focal irradiation, delivered by SRS or IMRT, can serve to ablate parenchymal cells in various organs and create a microenvironment that promotes the engraftment, growth and differentiation of progenitor/stem cell in vivo. The irradiation is thought to increase the engraftment by inhibiting the proliferation of endogenous cells, thereby leaving 'room' for the engrafted cells to grow.

The liver was used as our primary model organ. Adult liver cells (hepatocytes) have remarkable regenerative potential and have extensively repopulated rodent livers on serial transplantation (Overturf, K. et al., *Am J Pathol*, 151:1273-1280 (1997)). However, shortage of donor hepatocytes and inability to grow primary hepatocytes in culture have triggered a search for progenitor cells that can be grown in culture and cryopreserved in "cell banks" for future use. Accordingly, in exemplary embodiments where the liver is the target organ, the ex vivo cells are hepatic progenitor/stem cells—fetal hepatocytes, amniotic epithelial cells, "oval" cells and "small" hepatocytes. Fetal hepatocytes can differentiate into primary hepatocytes after intraportal cell transplantation. It is contemplated that the amniotic epithelial cells can maintain the plasticity of pregastrulation embryo cells and have the potential to differentiate to all three germ layers. Miki et al has recently demonstrated that amniotic epithelial cells isolated from human term placenta express surface markers normally present on embryonic stem and germ cells (Miki, T. et al., *Stem Cells*, 23:1549-1559 (2005)). In addition, amniotic epithelial cells express the pluripotent stem cell-specific transcription factors octamer-binding protein 4 (Oct-4) and nanog and can form spheroids that retain stem cell characteristics under certain culture conditions. They further demonstrate that amniotic epithelial cells do not require other cell-derived feeder layers to maintain Oct-4 expression, do not express telomerase, and are nontumorigenic upon transplantation. Based on immunohistochemical and genetic analysis, amniotic epithelial cells have the potential to differentiate to all three germ layers-endoderm (liver, pancreas), mesoderm (cardiomyocyte), and ectoderm (neural cells) in vitro. Thus, amnion derived from term placenta after live birth may be a useful and noncontroversial source of stem cells for cell transplantation and regenerative medicine. Accordingly, in one embodiment, the ex vivo cell is a amniotic epithelial cells which has the potential to engraft, differentiate and repopulate the host liver and rescue it from radiation injury.

Adult hepatic progenitor/stem cells (a.k.a. "oval" cells) expand during liver injury, such as, in alcoholic liver injury, and submassive parenchymal necrosis as well as experimental injury models featuring blocked hepatocyte replication, such as, after HIR. Oval cells can potentially become either hepatocytes or biliary epithelial cells and may be critical to liver regeneration, particularly when hepatocyte replication is impaired. Recently, it was reported that a TNF family member called TWEAK (TNF-like weak inducer of apoptosis) stimulates oval cell proliferation in mouse liver through its receptor Fn14 (Jakubowski, A. et al., *J Clin Invest*, 115:2330-2340 (2005)). Accordingly, in one embodiment, liver is treated with ex vivo "oval" cells and optionally, TWEAK is the mitogenic agent administered to rescue hepatic radiation injury by stimulating the proliferation of the transplated "oval" cells.

Figure 9:
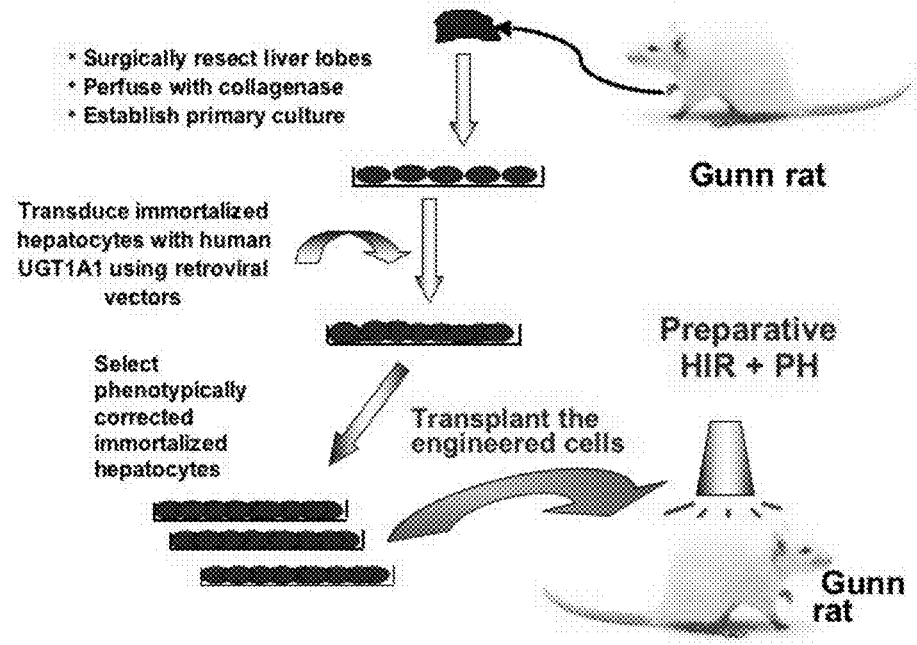
FIG. 9. Ex vivo UGT1A1 gene therapy in Gunn rats. A. Experimental design. B. UGT1A1 immuno-histochemistry demonstrating progressive repopulation of liver lobes by UGT1A1-transduced hepatocytes following PH+HIR at pre-transplant, 2 weeks, 4 weeks, 8 weeks, and 16 weeks. C. Complete correction of serum hyperbilirubinemia in Gunn rats after ex vivo gene therapy and transplantation of autologous, conditionally immortalized hepatocytes.
Figure 9:
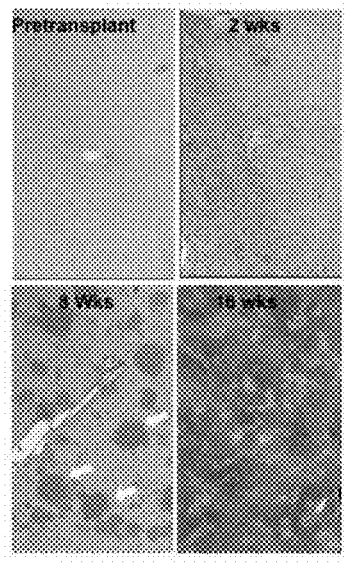
Figure 9:
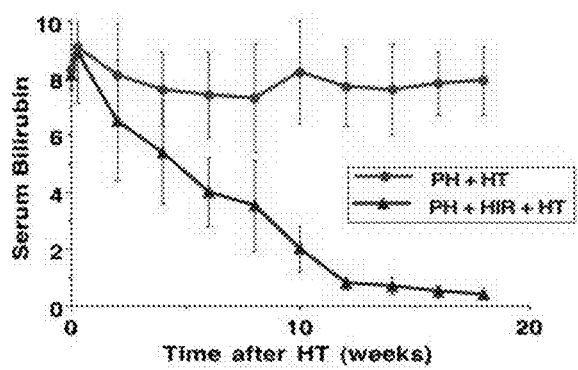

Finally, a "small hepatocyte" (SH) fraction has been described to have a better replicative potential than adult parenchymal hepatocytes (PaH) (Tateno, C. et al., *Hepatology*, 31:65-74 (2000); Katayama, S. et al., *Am J Pathol*, 158: 97-105 (2001)). SH can be isolated from the supernatant or the nonparenchymal component of collagenase-perfused rat liver. In experiments, we examined whether SH can repopulate faster than PaH. Extensive studies have been performed to evaluate the growth potential of a small hepatocyte population (<16 µm diameter) (Lemire, J. et al., *American Journal of Pathology*, 139:535-552 (1991)) isolated from the non-parenchymal fractions of collagenase-perfused livers (Kubota, H. et al., *Proc Natl Acad Sci USA*, 97:12132-12137 (2000); Sigal, S. et al., *Hepatology*, 19:999-1006 (1994); Sigal, S. et al., *Differentiation*, 59:35-42 (1995); Taniguchi, H. et al., *Cell Transplant*, 9:697-700 (2000); Yin, L. et al., *Hepatology*, 35:315-324 (2002); Suzuki, A. et al., *Hepatology*, 32:1230-1239 (2000); Fujikawa, T. et al., *J Hepatol*, 39:162-170 (2003)). These cells could proliferate in cell culture (Tateno, C. et al., *Hepatology*, 31:65-74 (2000), Tateno, C. et al., *Am J Pathol*, 149:1593-1605 (1996); Tateno, C. et al., *Am J Pathol*, 148:383-392 (1996); He, Z. et al., *Differentiation*, 71:281-290 (2003); Ikeda, S. et al., *J Hepatol*, 37:7-14 (2002)) and retained their proliferative capacity following long-term cryopreservation (Ikeda, S. et al., *J Hepatol*, 37:7-14 (2002)). It was reported that these cells have a higher proliferative capacity than adult parenchymal hepatocytes in the retrorsine+PH model of liver repopulation Katayama, S. et al., *Am J Pathol*, 158:97-105 (2001). In the context of clinical application, livers from adult donors contain very few oval cells, but a larger number of small hepatocytes can be isolated from the liver by Percoll gradient fractionation of liver cells. Our studies indicate that small hepatocytes may indeed have a better replicative potential than adult parenchymal hepatocytes (Section c.4.4, FIG. 9). Accordingly, in one embodiment where the liver is the target organ, the ex vivo cells are SH cells.

DEFINITIONS

Unless otherwise stated, the following terms used in the specification and claims have the meanings given below.

It is noted here that as used in this specification and the appended claims, the singular forms "a," "an," and "the" include plural reference unless the context clearly dictates otherwise.

Ex vivo cells—A mammalian cell capable of repopulating the host organ. They can be freshly harvested cells, cultured cells, and/or genetically transformed to provide a genetic marker, correct a genetic defect in the ex vivo cell (as in the case of some autologous ex vivo cells), or to increase or modulate their ability to proliferate when engrafted or in culture. In some embodiments, the host organ acts as a culture medium for the ex vivo cells. In some further embodiments, the cultured ex vivo cells can later be harvested for study or engraftment to another individual. In some embodiments, the ex vivo cell is a cell type whose function and/or number is deficient in the host organ. In some embodiments, the ex vivo cells is of the same cell type as that of the cell whose number or function is deficient in the host organ. In some embodiments, the ex vivo cell is a cell which can differentiate into such a cell. In some embodiments, the ex vivo cell is a cultured cell (e.g., one that can be passaged at least 25 or 50 times in culture). The ex vivo cell can be derived from the subject or another individual or another species. The ex vivo cell can be cultured to increase its population. In some embodiments, the cell is treated ex vivo to enhance a biological property (rate of mitosis, gene therapy) before being administered to the subject or engrafted onto the host. Ex vivo cells harvested from the host organ or host may be the subject of gene therapy and subsequently cultured to expand their population and then engrafted into or upon the host organ. Accordingly, the ex vivo cells can be adult somatic cells, adult progenitor cells, adult stem cells, embryonic progenitor cells, fetal cells, cord blood cells, xenogenic cells, or embryonic stem cells. The ex vivo cells can be fetal hepatocytes, amniotic epithelial cells, "oval" cells and "small" hepatocytes. In still other embodiments, the ex vivo cells are heterologous to the subject. In still other embodiments, the ex vivo cells are autologous to the subject. In additional embodiments, the ex vivo cells are the same cell type as an endogenous cell type of the organ or heterologous to the organ. In other embodiments, the ex vivo cells are not an endogenous cell type of the organ. The ex vivo cells can be cultured prior to administration. In some embodiments, the ex vivo cells express a heterologous nucleic acid for gene therapy. In some embodiments, the grafted cells repopulate the damaged organ with healthy cells of the same type and/or function as those whose growth was targeted to be disadvantaged, or disadvantaged, by administration of the agent that confers a growth disadvantage. In some embodiments, the cells are bone marrow progenitor cells, embryonic stem cells, neural progenitor cells, endothelial progenitor cells, progenitor cells obtained from peripheral blood, cord blood cells, amniotic epithelial cells, fetal cells, organ-specific stem cells, such as, oval cells, primary hepatocytes, primary parenchymal cells, human umbilical microvascular endothelial cells, blood outgrowth endothelial cells, glia, or human brain microvascular endothelial cells. In one embodiment, the ex vivo cell line is a highly differentiated immortalized human hepatocytes cell line (e.g., a highly differentiated immortalized human hepatocyte line with simian virus 40 large tumor antigen for liver based cell therapy, see, Li et al., ASAIO J. 51(3):262-8 (2005). Human progenitor liver epithelial cells with extensive replication capacity and differentiation into mature hepatocytes are also suitable (see, Yin et al., Stem Cells 20:338-346 (2002)). In some instances, an ex vivo cell (e.g., a stem cell) may fuse with an endogenous hepatocytes to provide the repopulated cell. The ex vivo cells may be administered locally or systemically. in some embodiments, the ex vivo cells are cryopreserved and stored for later use.

For instance, the ex vivo cells can be tissue stem cells which have the capacity to self-renew and are capable of producing progeny in at least two lineages. They can also be capable of long-term tissue reconstitution and serial transplantability.

Oval cells are liver stem cells which can either give rise to bile duct cells (cholangiocytes) or liver cells (hepatocytes). Whether or not the cells become cholangiocytes or hepatocytes depends on the pathophysiological circumstances they were grown under. Oval cells can be cryopreserved, stored and grown later.

In some embodiments, the ex vivo cells are bone marrow progenitor cells, embryonic stem cells, neural progenitor cells, endothelial progenitor cells, progenitor cells obtained from peripheral blood, cord blood cells, amniotic epithelial cells, fetal cells, organ-specific stem cells, such as, oval cells, primary hepatocytes, primary parenchymal cells, human umbilical microvascular endothelial cells, blood outgrowth endothelial cells, glia, or human brain microvascular endothelial cells.

In some embodiments, the ex vivo cell expresses a protein or polypeptide not normally expressed by the host tissue at the engraftment site and this protein is used as a label to detect the ex vivo cells. In some embodiments, the ex vivo cells are modified ex vivo to express a protein or provide a nucleic acid not normally expressed by the host or by tissues of the engraftment site or by the damaged organ or organ having a reduced function. In some embodiments, the modification introduces a gene which is expressed in other tissues of the host but which is not normally expressed at the engraftment site tissue or by the damaged organ. In some embodiments, the gene expresses creatine kinase and the damaged organ is the liver. The protein or nucleic acid can serve as a label by which the ex vivo cells and their progeny can be detected in the host. In some embodiments, the protein can be a fluorescent protein not otherwise expressed in the host. Detection of the ex vivo cells can be used to monitor the progress of the engraftment and to further adjust the regimens used to administer the agents which confers a growth disadvantage and/or mitogenic stimulus or to further administer additional ex vivo cells. A preferred method of evaluating host organ or engraftment site repopulation is taught by Landis et al., Hepatology 44:1250-1258 (2006), which is incorporated by reference in its entirety. This method discloses the use of magnetic resonance spectroscopic imaging detect ex vivo cells. Accordingly, in some embodiments, the ex vivo cells are detected using MRSI to detect substrates or products of reactions suitable for such imaging methods which are produced by enzymes which are differentially expressed by the ex vivo cells as opposed to the engraftment site tissues or damaged organ (e.g., $^{31}$P magnetic resonance spectroscopic imaging of liver engrafted with cells expressing creatine kinase). In some embodiments, the label is not otherwise expressed in the host and can be used to target the ex vivo cell for destruction by use of an antibody directed toward the protein in the event the ex vivo cells prove harmful to the host. Preferably, in this embodiment, the protein is expressed on the cell surface of the ex vivo cell. Methods of genetically modifying cells or making recombinant cells are well known to persons of ordinary skill in the art.

"Endogenous" cells are cells originating from the host and found in the target organ which may compete with ex vivo cells following their introduction for repopulating the organ.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all. In some embodiments according to the invention, the ex vivo donor cell has been modified by the introduction of a heterologous nucleic acid or protein or the alteration of a native nucleic acid or protein, or that the cell is derived from a cell so modified.

"Engraft" means to become established as a living part or attachment of a host organ. The graft may be orthotopic or heterotopic to the host organ.

Proliferation references the rate of cell division or multiplication and increase of cell number.

"Autologous" references biological mater derived from tissues or DNA of the subject or host. The ex vivo cells can be autologous.

"Heterologous" references biological matter derived from the tissues or DNA of a different species or different individual of the same species as the subject or host (e.g., allogenic or xenogenic). The ex vivo cells can be heterologous.

Agents that confer a growth disadvantage do not necessarily kill the cell, but competitively disadvantage the growth of the cell with respect to the engrafted ex vivo cells. The disadvantage is with respect to cellular proliferation rates and/or the ability of the endogenous cells to compete with the ex vivo cells in populating a host organ or survive. Such agents can be ionizing radiation, heat, ultrasound, LASAR, cytotoxic chemicals (preferably toxic chemicals which are selectively toxic for the endogenous cells of the target organ, and more particularly, the endogenous cells of the type to be repopulated. Ultrasound, focused ultrasound, focused ultrasound targeted by magnetic resonance imaging of the target site temperature, biological agents (viruses); cell growth suppressors. The agents may be cytostatic or cytotoxic. They may be biological agents, nucleic acids (e.g., siRNA) proteins (e.g., antibodies or polypeptides), drugs or small molecules that suppress cell division. Preferably, growth or cell proliferation of the endogenous cells can be reduced by at least 50%, 75%, 80%, 90%, 95% or 98% (or any range therebetween) of the rate observed for endogenous cells not so treated. The agents may be administered locally or systemically.

Mitogenic composition or mitogenic stimulus refer to subject matter that stimulates cell division such as a growth factor. One or more stimuli can be used. The stimulus can be a mitogen, chemokine, cytokine, hormone or agents which acts similarly on their receptors (e.g., antibodies). Preferred mitogens may be tissue specific and/or at least stimulate the ex vivo cell type to be engrafted. Suitable mitogens include mammalian growth factor (e.g., HGF, EGF, FGF, VEGF, NGF, 11-6, TNF-alpha, circulating tumour necrosis factor (CTNF), R-spondin 1, Noggin, and TWEAK, growth receptor ligand) and c-met activating antibody. EGF promotes proliferation of mesenchymal, glial and epithelial cells. NGF promotes neurite outgrowth and neural cell survival. FGF promotes proliferation of many cells; inhibits some stem cells; induces mesoderm to form in early embryos. FGF has at least 19 family members and 4 distinct receptors. Additional suitable mitogens include PDGF which promotes proliferation of connective tissue, glial and smooth muscle cells and has two different protein chains forming 3 distinct dimer forms; AA, AB and BB; insulin-like growth factor-I (IGF-I) which promotes proliferation of many cell types and is related to Insulin-like growth factor-II (IGF-II) and proinsulin, also called Somatomedin C; and IGF-II which promotes proliferation of many cell types primarily of fetal origin. The factors may be wild-type (e.g, human, primate, murine, rat, etc.) or substantially identical to the wild-type factor. Preferably, cell growth rates are increased by at least 1.5-fold, 2-fold, 3-fold, 4-fold, or 6-fold (or any range therebetween). The compositions or stimuli may be administered locally or systemically. PDGF promotes proliferation of connective tissue, glial and smooth muscle cells. Two different protein chains form 3 distinct dimer forms; AA, AB and BB. Osteoinductive molecules are one or more of the following: BMP-1, BMP-2, BMP-3, BMP-4, BMP-5, BMP-6, BMP-7, BMP-8, BMP-9, BMP-10, BMP-11, BMP-12, BMP-13, BMP-14, BMP-15 and BMP-16. The stimulus may be a heterologous gene that increases their intrinsic proliferation capacity or survival. The mitogenic stimulus may comprise a biological agent, antibody or peptide factor that increases the proliferation capacity of the donor cells or a procedure that deliberately injures the engraftment site to make "space" for the engrafted ex vivo cells and/or to provide a compensatory growth signal for the ex vivo cells.

"Repopulate" means that the engrafted ex vivo cells grow to provide or replace at least 5%, 10%, 20%, 30%, 40%, 50%, 60%, 70%, 80%, 90%, or 95% (or any range represented therebetween) of the cells of the damaged organ. The cells to be replaced may be of the same tissue type as the engrafted cells. "Repopulate" also references a cell population which is sufficient in number and activity to ameliorate a condition associated with the damage to the organ or improve a homeostasis (e.g., metabolism of glucose, ammonia, blood lipids, etc.) originally impaired by the damage to the organ. The repopulation by the ex vivo cells typically can provide organ specific parenchymal cells. The ex vivo cell can be homologous or heterologous to the organ.

"Effective amount" or "effective dose" or "therapeutically sufficient or effective amount or dose" and the like reference a dose of an agent, mitogenic compound, or ex vivo cell that produces the intended effect for which it is administered. The exact dose will depend on the purpose of the treatment, and can be ascertainable by one skilled in the art using known techniques. An intended effect of the agent which confers a growth disadvantage on the endogenous cells is just that. An intended effect of a mitogen is to repopulate the target organ with the ex vivo cells. An intended effect of the ex vivo cell is to restore or maintain a homeostasis effected by the target organ. Methods of tracing the origin of cell populations and assessing homeostatis are well known in the transplantation and clinical arts.

An "organ" is a group of tissues that perform a specific function or group of functions. Usually there are main tissues and their cell types that uniquely predominate for the specific organ and sporadic tissues and cell types. For example, in the brain the main tissues are neurons and glia and sporadic tissues include the blood and endothelium of the blood vessel wall. Organs which may be treated according to the invention include the lungs, brain, eye, skin, stomach, spleen, bone, pancreas, kidneys, liver, intestines, skin, uterus, and bladder, prostate, ear, and testes. An exemplary organ according to the invention is the liver. Accordingly, the ex vivo cells can repopulate an organ to provide cells of a desired type including those of the following tissues: bone, cartilage, ligament, tendon, heart, liver, kidney, brain, skin, cartilage, bladder, lung, thymus, thyroid, spinal cord, pancreas, skin, gut, bowel, blood vessels, bladder, joint cartilage, intervertebral disc, ligament, tendon, meniscus, or pancreas.

A "damaged organ" or "organ having a reduced function" is one which has lost a substantial portion of its biological functioning and/or mass due to the damage. The damage can be due to trauma, surgery, infection, cancer, congenital or genetic condition, or a chemical exposure. The damage may relate to the ability to provide a needed product (e.g., glucose, insulin, secretion, signal) or function (e.g., metabolize drugs, motility, filtration, excretion). In some embodiments, there is a proviso that the damage to be treated is one which was not itself caused by exposure to the agent to be used to confer the growth disadvantage. In other embodiments, there is a proviso that the damaged organ is not the pancreas and/or bone marrow. One of ordinary skill in the clinical art can recognize a subject having a damaged organ or an organ having a reduced function and who, accordingly, would benefit from treatments according to the invention. Further, one of ordinary skill in the clinical arts can ascertain when a function impaired by the damage to the host organ or tissue has been ameliorated, improved, or restored by use of appropriate clinical endpoints.

A "host" or "target" organ is one to be populated or repopulated with ex vivo cells. It may be the same organ type from which the ex vivo cells were derived or different. For instance, ex vivo hepatocytes may be engrafted onto the spleen. In an exemplary embodiment, the host organ is the liver, and the ex vivo cells are capable of repopulating the liver with hepatocytes.

A subject references a mammal and includes human and non-human animals (e.g., primates, rodents, lagomorphs, pigs). An exemplary subject is the human.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Methods for obtaining (e.g., producing. isolating, purifying, synthesizing, and recombinantly manufacturing) polypeptides are well known to one of ordinary skill in the art.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As to "conservatively modified variants" of amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

"Nucleic acid" or "polynucleotide" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions)

and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

Polynucleotides may comprise a native sequence (i.e., an endogenous sequence that encodes an individual antigen or a portion thereof) of a protein of interest or may comprise a variant of such a sequence as set forth above. Polynucleotide variants may contain one or more substitutions, additions, deletions and/or insertions such that the biological activity of the encoded chimeric protein is not diminished, relative to a chimeric protein comprising native antigens. Variants preferably exhibit at least about 70% identity, more preferably at least about 80% identity and most preferably at least about 90%, 95%, 96%, 97%, 98% or 99% identity to a polynucleotide sequence that encodes a native polypeptide or a portion thereof.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

An "expression cassette" refers to a polynucleotide molecule comprising expression control sequences operatively linked to coding sequence(s).

A "vector" is a replicon in which another polynucleotide segment is attached, so as to bring about the replication and/or expression of the attached segment.

"Control sequence" or "control element" refers to polynucleotide sequences which are necessary to effect the expression of coding sequences to which they are ligated. The nature of such control sequences differs depending upon the host organism; in prokaryotes, such control sequences generally include promoter, ribosomal binding site, and terminators; in eukaryotes, generally, such control sequences include promoters, terminators and, in some instances, enhancers. The term "control sequences" is intended to include, at a minimum, all components whose presence is necessary for expression, and may also include additional components whose presence is advantageous, for example, leader sequences.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Conservatively modified variants" also applies to nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

The terms "identical" or percent "identity," in the context of two or more nucleic acids or polypeptide sequences, including siRNA and polypeptides, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to the full length of the reference sequence, usually about 25 to 100, or 50 to about 150, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man in the laboratory is naturally-occurring.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., John Wiley & Sons.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec.-2 min., an annealing phase lasting 30 sec.-2 min., and an extension phase of about 72° C. for 1-2 min. Protocols and guidelines for low and high stringency amplification reactions are provided, e.g., in Innis et al., *PCR Protocols, A Guide to Methods and Applications*, Academic Press, Inc. N.Y. (1990)).

The term "heterologous" when used with reference to a protein or a nucleic acid indicates that the protein or the nucleic acid comprises two or more sequences or subsequences which are not found in the same relationship to each other in nature. For instance, the nucleic acid is typically recombinantly produced, having two or more sequences from unrelated genes arranged to make a new functional nucleic acid. For example, in one embodiment, the nucleic acid has a promoter from one gene arranged to direct the expression of a coding sequence from a different gene. Thus, with reference to the coding sequence, the promoter is heterologous. Similarly, a heterologous protein indicates that the protein comprises two or more subsequences that are not found in the same relationship to each other in nature (e.g., a fusion protein). "Heterologous" accordingly includes those proteins and polynucleotide sequences which are not found in a cell in which they are introduced. Such proteins can be of mammalian, primate, human, reptilian, or insect origin.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under-expressed or not expressed at all. Methods of making recombinant cells using vectors, promoters, and other gene regulatory agents, and nucleic acids encoding heterologous proteins of interest are well known to persons of ordinary skill in the art.

The term "isolated" with regard to polypeptide or peptide fragment or polynucleotides as used herein refers to a polypeptide or a peptide fragment or polynucleotide which either has no naturally-occurring counterpart or has been separated or purified from components which naturally accompany it, e.g., in normal tissues such as lung, kidney, or placenta, tumor tissue such as colon cancer tissue, or body fluids such as blood, serum, or urine. Typically, the polypeptide or peptide fragment or polynucleotide is considered "isolated" when it is at least 70%, by dry weight, free from the proteins and other naturally-occurring organic molecules with which it is naturally associated. Preferably, a preparation of a polypeptide (or peptide fragment thereof) or polynucleotide of the invention is at least 80%, more preferably at least 90% or 95%, and most preferably at least 99%, by dry weight, the polypeptide (or the peptide fragment thereof), or polynucleotide, respectively, of the invention. Thus, for example, a preparation of polypeptide x is at least 80%, more preferably at least 90%, and most preferably at least 99%, by dry weight, polypeptide x. Since a polypeptide or polynucleotide that is chemically synthesized is, by its nature, separated from the components that naturally accompany it, the synthetic polypeptide is "isolated."

Once a recombinant chimeric protein is expressed, it can be identified by assays based on the physical or functional properties of the product, including radioactive labeling of the product followed by analysis by gel electrophoresis, radioimmunoassay, ELISA, bioassays, etc.

In some embodiments, the mitogenic stimulus or agent conferring a growth disadvantage can be an antibody. Antibodies can also be used to detect or target ex vivo cells engrafted in the host. The targeting can be for the purpose of killing a cell which has proved harmful. "Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993)). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature,* 348:552-554 (1990)).

For preparation of antibodies, e.g., recombinant, monoclonal, or polyclonal antibodies, many technique known in the art can be used (see, e.g., Kohler & Milstein, *Nature,* 256:495-497 (1975); Kozbor et al., *Immunology Today,* 4:72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology,* 10:779-783 (1992); Lonberg et al., *Nature,* 368:856-859 (1994); Morrison, *Nature,* 368:812-13 (1994); Fishwild et al., *Nature Biotechnology,* 14:845-51 (1996); Neuberger, *Nature Biotechnology,* 14:826 (1996); and Lonberg & Huszar, *Intern. Rev. Immunol.,* 13:65-93 (1995)). Alternatively, phage display technology can be used to identify antibodies and heteromeric Fab fragments that specifically bind to selected antigens (see, e.g., McCafferty et al., *Nature,* 348:552-554 (1990); Marks et al., Biotechnology, 10:779-783 (1992)). Antibodies can also be made bispecific, i.e., able to recognize two different antigens (see, e.g., WO 93/08829, Traunecker et al., *EMBO J.*, 10:3655-3659 (1991); and Suresh et al., *Methods in Enzymology*, 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature*, 321:522-525 (1986); Riechmann et al., *Nature*, 332:323-327 (1988); Verhoeyen et al., *Science*, 239:1534-1536 (1988) and Presta, *Curr. Op. Struct. Biol.*, 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

Methods of Conferring a Growth Disadvantage

Irradiation can be used to confer a growth disadvantage on endogenous cells of the target organ. For instance, toward the development of a clinically applicable approach to liver repopulation, we have explored preparative hepatic irradiation (HIR) to injure host hepatocytes and prevent them from proliferating and competing with donor hepatocytes in response to mitotic stimuli. Preparative irradiation is routinely used for bone marrow transplantation (Thomas, E. et al., *N Engl J Med*, 292:832-843 (1975)), but we were the first to use HIR to facilitate HT in rodent models (Guha, C. et al., *Int J Radiat Oncol Biol Phys*, 49:451-457 (2001); Guha, C. et al., *Artif Organs*, 25:522-528 (2001); Guha, C. et al., *Hepatology*, 36:354-362 (2002); Takahashi, M. et al., *Gene Ther*, 10:304-313 (2003); Guha, C. et al., *Cancer Res*, 59:5871-5874 (1999)). Ionizing radiation (IR) induces apoptosis of bone marrow cells and thereby, makes "room" for donor cell engraftment. Our results demonstrate that HIR in combination with a compensatory hepatic regenerative stimuli, such as, partial hepatectomy (PH) (Guha, C. et al., *Hepatology*, 36:354-362 (2002); Guha, C. et al., *Cancer Res*, 59:5871-5874 (1999)), Fas-induced apoptosis (Takahashi, M. et al., *Gene Ther*, 10:304-313 (2003)), or portal vein branch ligation (Deb, N. et al., *Hepatology*, 34 (4):153A., 34:153A (2001)), or a direct mitotic stimuli, provided by hepatotropic growth factors, such as, thyroid hormone (Parashar, B. et al., *Hepatology*, 32:206A (2000)), or hepatocyte growth factor (HGF) (Guha, C. et al., *Am J Nephrol*, 25:161-170 (2005)) induces extensive repopulation of transplanted hepatocytes in the host liver. We have demonstrated that HIR, in combination with proliferative stimuli for hepatocytes, could potentially suppress host hepatocellular proliferation and induce post-mitotic death, thus making "room" for donor hepatocytes that preferentially proliferate and repopulate the irradiated host liver. HIR can be safely administered in the clinic using stereotactic radiosurgery (SRS) or 3-D conformal RT (3-D CRT) techniques and can be used as a preparative regimen for HT. Thus, preparative HIR can facilitate HT for i) the treatment of inherited liver diseases, ii) ex vivo hepatic gene therapy, iii) rescuing patients with liver cancer, following chemotherapy or radiation therapy, or other liver damage; and iv) expanding human hepatocytes in animal liver for generating animal models for human-specific infections (Table 1).

First, although PH provided the mitotic signal in our initial repopulation experiments, a non-invasive substitute to PH is more desirable for clinical application. Accordingly, we have examined whether HIR in combination with hepatic growth factors, such as, HGF and EGF, could promote repopulation of transplanted hepatocytes. Use of an activating antibody to the HGF receptor, c-met, to promote selective proliferation of hepatocytes in the irradiated liver is also contemplated. Second, radiation-induced liver injury is a function of mean liver dose and the irradiated liver volume (Lawrence, T. et al., *International Journal of Radiation Oncology, Biology, Physics*, 19:1041-1047 (1990); Dawson, L. et al., *Int J Radiat Oncol Biol Phys*, 53:810-821 (2002)) in humans. A lower dose of HIR, or partial liver irradiation is desirable for clinical application of HIR. Partial liver irradiation is well tolerated in cancer patients and with modern techniques of IMRT, doses higher than 50 Gy to parts of the liver can safely be offered to patients in the clinic. Our initial studies demonstrate that HIR administered to the anterior lobes of the liver can induce selective lobar repopulation of donor cells (Deb, N. et al., *Hepatology*, 34 (4):153A., 34:153A (2001)). It is accordingly contemplated that partial liver irradiation along with hepatic growth factors can be used in preparative regimens of HT.

TABLE 1

The scope of liver cell transplantation
and hepatocyte-based gene therapy

A. REPLACEMENT OF A MISSING GENE PRODUCT
Liver manifests disease
Genetic Disorders Wilson's disease
Lipidoses, e.g., Niemann-Pick disease
Tyrosinemia Type I
Protoporphyria
Ornithine transcarbamylase deficiency
B. MASSIVE REPLACEMENT OF HOST HEPATOCYTES THAT
EXPRESS AN OFFENDING GENE
C. REPLACE DISEASED HEPATOCYTES:

AMELIORATION OF RT/DRUG-INDUCED LIVER INJURY
"BRIDGE" TO OLT IN LIVER FAILURE PATIENTS
D. EXPRESSION OF GENES THAT ARE NORMALLY NOT
EXPRESSED IN THE LIVER

Hormones, e.g., insulin, immunosuppressive Genes, anti-angiogenic
agents, cytokine immunomodulation (for suppressing tumor growth)
Extrahepatic organs manifest disease
Metabolic deficiency disorders Crigler-Najjar Syndrome
Familial hypercholesterolemia
Defects in carbohydrate metabolism
Coagulation Disorders Hemophilia A & Factor IX deficiency
Primary hyperoxaluria
α-1 antitrypsin deficiency (mutant A1AT)
Acute liver failure
Chronic viral hepatitis and cirrhosis
Drug or Radiation-induced liver injury in cancer patients
E. DEVELOPMENT OF HUMAN-MOUSE LIVER CHIMERA/
GENERATION OF ANIMAL MODELS OF HUMAN-SPECIFIC
INFECTIONS Malaria
Viral Hepatitis Additionally, the invention provides methods of pretreating an organ to reduce the growth or proliferation of endogenous cells of the organ by administering an agent selectively or predominantly toxic to the endogenous cells of the organ as opposed to other organs. The toxic effects and target organs for a variety of chemicals are disclosed in Registry of Toxic Effects of Chemical Substances (RTECS), RTECS (NIOSH 1980 or later editions, including 1995). RTECS is a database of toxicity information compiled from the published scientific literature. Prior to 2001, RTECS was maintained by US National Institute for Occupational Safety and Health (NIOSH). Now, it is maintained by Elsevier MDL. See, also, Olson et al. Ed., Poisoning and Drug Overdose, 5th Edition, published by McGraw Hill/Lange for a listing of toxic agents and their effects and target organs. For instance, as to the liver, some halogenated compounds and carcinogens which are selectively or principally toxic for the liver may be used.

Methods of Engrafting and Repopulating
Ex Vivo Cell Isolation.

Cells can be isolated with a modified collagenase perfusion method from a mammalian organ or tissue, as originally described by Berry and Friend (Takahashi, M. et al., *Gene Ther*, 10:304-313 (2003)). After dissociation, cells can be filtered through a Dacron mesh of a dimension corresponding to the cell of interest and then washed twice at 50×g for 1 min each. Cell viability can be determined by trypan blue dye exclusion. Cells with >90% viability can be used for transplantation. Ex vivo cells can be adult somatic cells, adult progenitor cells, adult stem cells, embryonic progenitor cells, or embryonic stem cells. Sources of such cells are well known to persons of ordinary skill in the art. For example, with regard to the liver, hepatocytes can be isolated with a modified collagenase perfusion method using male F344 rats, as originally described by Berry and Friend (Takahashi, M. et al., *Gene Ther*, 10:304-313 (2003)). After liver dissociation, cells were filtered through an 80-μm Dacron mesh and washed twice at 50×g for 1 min each. Cell viability can be determined by trypan blue dye exclusion. Hepatocytes with >90% viability were used for transplantation (see, also, Guha, C. et al., *Cancer Research* 59, 5871-5874, (1999) and, also, Nowak, G., et al., *Gut* 54:972-979 (2005)).

Administration of Ex Vivo Cells

Ex vivo cells are introduced into the subject in a number which depends upon the species and organ to be engrafted and the extent of the need for such therapy. Ex vivo cells can be injected directly into the spleen, kidney capsule, or target organ of the subject as described previously (Guha, C. et al., *Artif Organs*, 25:522-528 (2001)) or administered intraperitoneally or other site of engraftment. They may also be administered intravenously or intraportally (in the case of the liver). For instance, when administering hepatocytes to the rat, under ether anesthesia, the spleen can be exposed, and $5\times10^6$ hepatocytes suspended in 0.5 ml of RPMI 1640 can be injected into the splenic pulp. Generally, hepatocytes can be administered in suitable media providing single or divided doses of from $1\times10^5$ to $5\times10^9$ cells per treatment. Total dosages, administered singly or as a divided dose, may be from 1 from $1\times10^5$ to $5\times10^{10}$ ex vivo cells/kg of body weight; in some embodiments the total dosages, administered singly or as a divided dose, may be from 1 from $1\times10^6$ to $1\times10^9$ ex vivo cells/kg of body weight; in some embodiments the total dosages, administered singly or as a divided dose, may be from 1 from $1\times10^7$ to $5\times10^8$ ex vivo cells/kg of body weight.

Methods of Determining Engraftment
Histological Analysis.

By methods known to one of ordinary skill in the art, engrafted ex vivo cells can be distinguished from endogenous cells by the use of antigenic markers, identifying chromosomal or genomic nucleic acid sequence differences between the engrafted and endogenous cells, fluorescent markers such as GFP, or enzymatic markers such as DPPIV, or according to a functional enzyme present in the ex vivo cell and deficient in the host endogenous cells. Sections of an organ can be embedded in OCT, frozen in liquid nitrogen, and stored at −70° C. or fixed in formalin for paraffin embedding and standard H&E staining. For the liver, Reticulin and trichrome stains can be performed in a standard histopathology laboratory. Ex vivo cells can be distinguished from endogenous cells by the use of antigenic markers, identifying chromosomal or genomic nucleic acid sequence differences between the engrafted and endogenous cells, fluorescent markers such as GFP, or enzymatic markers such as DPPIV, or according to a functional enzyme present in the ex vivo cell and deficient in the host endogenous cells. For instance, in the case of DPPIV marked ex vivo cells, DPPIV activity in situ can be assessed using 5-μm-thick cryostat sections fixed in chloroform and acetone (1:1, v/v) for 10 min at 40° C., as described previously (Guha, C. et al., *Cancer Res*, 59:5871-5874 (1999)). After air drying, sections can be incubated for 30 min at room temperature in a solution containing 0.4 mg glycyl-L-proline-4-methoxy-2-naphthylamide, along with 1 mg Fast Blue B salt in PBS (pH 7.4) and the fluorescent reaction products detected. The reaction can be terminated by washing with water and sections and counterstaining with hematoxylin.

A variety of model systems can be used to detect engraftment and repopulation of donor hepatocytes. For instance, one can use a mouse model, where transgenic beta-galactosidase (β-gal)-expressing (Rosa) C57Bl/6 hepatocytes are transplanted into wild-type C57Bl/6 mice. Or, DPPIV+ve F344 hepatocytes can be transplanted into congeneic, DPPIV-ve F344 host liver. Since DPPIV is highly expressed in the bile canalicular domain of the hepatocytes, the transplanted cells can easily be detected by enzyme histochemistry. In addition, after characterizing a noninvasive, robust, preparative regimen of hepatocyte repopulation, one can further examine its effectiveness in ameliorating a rodent model of metabolic liver disease, such as the Gunn rat, which is a model for Crigler-Najjar syndrome. Experiments can be simultaneously performed in more than one species. Initial dose of HIR would be 50 Gy, which has been very effective in inducing donor cell proliferation in our studies and is safe in rodents. One can perform a dose response study of HIR (e.g., 10, 20, 30 and 50 Gy), in order to identify the lowest dose of HIR that permits effective donor cell repopulation. To investigate the nature of radiation injury to the host hepatocytes, experiments can also be performed with mice that received HIR and HGF without HT. Animals from various cohorts can be sacrificed at various time points (1 d, 2 d, 3 d, 1 wk, 3 wk, 6 wk and 12 wk) and liver sections can be stained with H&E for histopathological analysis. BrdU and TUNEL staining can be performed for examining hepatocyte proliferation and apoptosis, respectively.

Organ Function Tests

In the clinical setting, engraftment can be assessed by biopsy with analyses as described above. Additionally, clinical tests can be used to assess the extent to which homeostasis is supported by the engrafted organ. Improvement in one or more clinical parameters related to the functioning of a target or engrafted organ can be used to indirectly assess the efficacy of the engraftment. Suitable clinical tests will vary with respect to the organ. With regard to the liver, standard liver function tests which monitor blood levels of any of alanine aminotransferase; spartate aminotransferase; alkaline phosphatase; gamma-glutamyltransferase, bilirubin, or ammonia may be used.

i) Donor Hepatocyte Engraftment and Repopulation.

Donor cells can be identified by beta-galactosidase and DPP IV histochemistry in C57Bl/6 mice and DPP IV-ve, F344 rats, respectively. To demonstrate the engraftment of transplanted cells, double staining for beta-galactosidase and ATPase in the rosa/Bl6 model or for DPPIV and ATPase in the DPP IV-ve can be performed in the F344 model. Donor cell proliferation in DPPIV-ve rats can be determined by co-localization of DPPIV activity (histochemistry) and immunostaining for BrdU incorporation in the nuclei, according to previously published methods (Gupta, S. et al., *Proceedings of the National Academy of Sciences of the United States of America*, 92:5860-5864 (1995)).

ii) Physiological Function of Repopulated Hepatocytes.

The ability of transplanted cells to perform unique hepatocyte biochemical functions, albumin synthesis (albumin immunostaining), glucose metabolism (stain for glucose-6-phosphatase) and gluconeogenesis (glycogen staining) can be examined in fresh frozen section according to published protocols (Laconi, E. et al., *Am J Pathol*, 153:319-329 (1998)). In Gunn rats, amelioration of hyperbilirubinemia can be used to indicate the degree of repopulation and the physiological function of the transplanted hepatocytes. At various time points (1, 2, 3 and 6 months), animals can be sacrificed and the function of the engrafted normal hepatocytes can be evaluated by measuring UGT1A1 activity in liver biopsy specimens, performing immunoblot analysis of UGT1A1 and immunohistochemistry to detect donor UGT1A1+ve hepatocytes and by determining the excretion of bilirubin glucuronides in bile.

iii) Toxicities of the Preparative Regimens.

As described in our publications (Guha, C. et al., *Hepatology*, 36:354-362 (2002); Guha, C. et al., *Cancer Res*, 59:5871-5874 (1999); Nakatani, T. et al., *J Biol Chem*, 277: 9562-9569 (2002)), serum albumin, transferrin, AST, ALT, GGT, GST-pi and alpha-feto protein (AFP) can be measured to examine the normal physiological functions of the repopulated hepatocytes and to determine any potential manifestations of radiation injury and tumorigenesis at the end of experiments. H & E staining of the liver biopsies can be performed to examine for histopathological evidence of hepatic radiation injury and tumorigenesis.

Gene Therapy

In some embodiments, the ex vivo cell to be engrafted is a recombinant cell transduced or transformed ex vivo to express a protein or to have increased ability to compete with endogenous cells upon engrafting or to grow in culture. In some embodiments, the protein may function as a marker, to provide a function deficient in the host organ or to modulate the growth and/or survival of the ex vivo cell (e.g., may provide a mitogenic stimuli to growth of the ex vivo cells). The nucleic acid expressing the genome is operably linked to regulatory elements which may be introduced or transduced into the cell by conventional means which are well known in the art. Construction of suitable vectors containing the desired gene coding and control sequences employs standard ligation and restriction techniques, which are well understood in the art (see Maniatis et al., in Molecular Cloning: A Laboratory Manual, Cold Spring Harbor Laboratory, New York (1982)). Isolated plasmids, DNA sequences, or synthesized oligonucleotides are cleaved, tailored, and religated in the form desired. The regulatory elements may be in turn regulated by agents which are subject to manipulation in the host (e.g., heat shock promoters or A variety of viral and non-viral delivery vectors useful to achieve expression of nucleotide sequences in transduced cells are known in the art. See, e.g. Boulikas, T in *Gene Therapy and Molecular Biology, Volume* 1 (Boulikas, T. Ed.) 1998 Gene Therapy Press, Palo Alto, Calif. pages 1-172. Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in, e.g., U.S. Pat. No. 5,049,386, U.S. Pat. No. 4,946,787; and U.S. Pat. No. 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration). A targeting construct for knocking the desired first gene into another second gene having suitable expression can be a replacement vector designed to replace the second gene coding sequences with those of the first (see, Yin et al, *Stem Cells* 20:338-346 (2002). As indicated in the Examples, genes may also be modified using viral vectors as known in the art.

Examples of non-viral delivery systems used to introduce a gene to a target cell include expression plasmids capable of directing the expression of the protein. Expression plasmids are autonomously replicating, extrachromosomal circular DNA molecules, distinct from the normal genome and nonessential for cell survival under nonselective conditions capable of effecting the expression of a DNA sequence in the target cell. The expression plasmid may also contain promoter, enhancer or other sequences aiding expression of the therapeutic gene and/or secretion can also be included in the expression vector. Additional genes, such as those encoding drug resistance, can be included to allow selection or screening for the presence of the recombinant vector. Such additional genes can include, for example, genes encoding neomycin resistance, multi-drug resistance, thymidine kinase, beta-galactosidase, dihydrofolate reductase (DHFR), and chloramphenicol acetyl transferase.

The expression plasmid containing the gene may be encapsulated in liposomes. Liposomes include emulsions, foams, micelles, insoluble monolayers, liquid crystals, phospholipid dispersions, lamellar layers and the like. The delivery of nucleic acids to cells using liposome carriers is well known in the art. A variety of methods are available for preparing liposomes, as described in, e.g., Szoka et al. Ann. Rev. Biophys. Bioeng. 9:467 (1980), Szoka, et al. U.S. Pat. No. 4,394,448 issued Jul. 19, 1983, as well as U.S. Pat. Nos. 4,235,871, 4,501,728, 4,837,028, and 5,019,369. Liposomes useful in the practice of the present invention may be formed from one or more standard vesicle-forming lipids, which generally include neutral and negatively charged phospholipids and a sterol, such as cholesterol. Examples of such vesicle forming lipids include DC-chol, DOGS, DOTMA, DOPE, DOSPA, DMRIE, DOPC, DOTAP, DORIE, DMRIE-HP, n-spermidine cholesterol carbamate and other cationic lipids as disclosed in U.S. Pat. No. 5,650,096. The selection of lipids is generally guided by consideration of, e.g., liposome size, acid lability and stability of the liposomes in the blood stream. Additional components may be added to the liposome formulation to increase serum half-life such as polyethylene glycol coating (so called "PEG-ylation") as described in U.S. Pat. No. 5,013,556 issued May 7, 1991 and U.S. Pat. No. 5,213,804 issued May 25, 1993.

In order to provide directed delivery of the non-viral gene to a particular cell, it may be advantageous to incorporate elements into the non-viral delivery system which facilitate cellular targeting. For example, a lipid encapsulated expression plasmid may incorporate modified surface cell receptor ligands to facilitate targeting.

In one embodiment of the invention as exemplified herein, the vector is a viral vector. The terms virus(es) and viral vector(s) are used interchangeably herein. The viruses useful in the practice of the present invention include recombinantly modified enveloped or non-enveloped DNA and RNA viruses, preferably selected from baculoviridiae, parvoviridiae, picornoviridiae, herpesveridiae, poxyiridae, adenoviridiae, or picornnaviridiae. The viral genomes may be modified by conventional recombinant DNA techniques to provide expression of the gene and may be engineered to be replication deficient, conditionally replicating or replication competent. Chimeric viral vectors which exploit advantageous elements of each of the parent vector properties (See e.g., Feng, et al. (1997) Nature Biotechnology, 15:866-870) may also be useful in the practice of the present invention. Minimal vector systems in which the viral backbone contains only the sequences needed for packaging of the viral vector and may optionally include a gene expression cassette may also be employed in the practice of the present invention. In some instances it may be advantageous to use vectors derived from different species from that to be treated which possess favorable pathogenic features such as avoidance of pre-existing immune response. For example, equine herpes virus vectors for human gene therapy are described in WO98/27216 published Aug. 5, 1998. The vectors are described as useful for the treatment of humans as the equine virus is not pathogenic to humans. Similarly, ovine adenoviral vectors may be used in human gene therapy as they are claimed to avoid the antibodies against the human adenoviral vectors. Such vectors are described in WO 97/06826 published Apr. 10, 1997.

Many viruses exhibit the ability to infect a broad range of cell types. However, in some applications it may be desirable to infect only a certain subpopulation of cells. Consequently, a variety of techniques have evolved to facilitate selective or "targeted" vectors to result in preferential infectivity of the mature viral particle of a particular cell type. Cell type specificity or cell type targeting may also be achieved in vectors derived from viruses having characteristically broad infectivity such as adenovirus by the modification of the viral envelope proteins. For example, cell targeting has been achieved with adenovirus vectors by selective modification of the viral genome knob and fiber coding sequences to achieve expression of modified knob and fiber domains having specific interaction with unique cell surface receptors.

In one embodiment of the invention as exemplified herein, the vector is an adenoviral vector. The use of adenoviral vectors for the delivery of exogenous transgenes are well known in the art. See e.g., Zhang, W-W. Cancer Gene Therapy, 6:113-138 (1999). Vectors can also be derived from the adenoviral, adeno-associated viral and retroviral genomes. In the most preferred practice of the invention, the vectors are derived from the human adenovirus genome. The replicative capacity of such vectors may be attenuated (to the point of being considered "replication deficient") by modifications or deletions in the E1a and/or E1b coding regions.

The viral genome may be modified to include inducible promoters which achieve replication or expression only under certain conditions. Examples of inducible promoters are known in the art (See, e.g. Yoshida and Hamada, Biochem. Biophys. Res. Comm., 230:426-430 (1997); Lida, et al., J. Virol., 70(9):6054-6059 (1996); Hwang, et al., J. Virol, 71(9): 7128-7131 (1997); Lee, et al., Mol. Cell. Biol., 17(9):5097-5105 (1997); and Dreher, et al., J. Biol. Chem., 272(46); 29364-29371 (1997). The viruses may also be designed to be selectively replicating viruses such as those described in Ramachandra, et al. PCT International Publication No. WO 00/22137, International Application No. PCT/US99/21452 published Apr. 20, 2000 and Howe, J., PCT International Publication No. WO WO0022136, International Application No. PCT/US99/21451 published Apr. 20, 2000. The virus may also be modified to be attenuated for replication in certain cell types. For example the adenovirus dl1520 containing a specific deletion in the E1b55K gene (Barker and Berk (1987) Virology 156: 107) has been used with therapeutic effect in human beings. Such vectors are also described in McCormick (U.S. Pat. No. 5,677,178 issued Oct. 14, 1997) and McCormick, U.S. Pat. No. 5,846,945 issued Dec. 8, 1998.

Methods of Administration and Pharmaceutical Compositions of Active Agents

The pharmaceutically active agents, including but not limited to pharmaceutical agents which disadvantage the endogenous cells with respect to the engrafted ex vivo cells, the mitogenic compositions, and immunosuppressive agents for use according to the invention can be administered to a subject in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of biopolymers is preferred. The administration may be local or systemic.

The compositions for administration will commonly comprise the active agent as described herein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

Thus, a typical pharmaceutical composition for intravenous administration will vary according to the active agent. Actual methods for preparing parenterally administrable compositions will be known or apparent to those skilled in the art and are described in more detail in such publications as Remington: The Science and Practice of Pharmacy, 20th ed., Lippincott, Williams, and Wilkins, (2000).

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that antibodies when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

Pharmaceutical formulations can be prepared by mixing an active agent having the desired degree of purity with optional pharmaceutically acceptable carriers, excipients or stabilizers. Such formulations can be lyophilized formulations or aqueous solutions. Acceptable carriers, excipients, or stabilizers are nontoxic to recipients at the dosages and concentrations used. Acceptable carriers, excipients or stabilizers can be acetate, phosphate, citrate, and other organic acids; antioxidants (e.g., ascorbic acid) preservatives low molecular weight polypeptides; proteins, such as serum albumin or gelatin, or hydrophilic polymers such as polyvinylpyllolidone; and amino acids, monosaccharides, disaccharides, and other carbohydrates including glucose, mannose, or dextrins; chelating agents; and ionic and non-ionic surfactants (e.g., polysorbate); salt-forming counter-ions such as sodium; metal complexes (e.g. Zn-protein complexes); and/or non-ionic surfactants.

The compositions can be administered in a "therapeutically effective dose." Single or multiple administrations of the compositions may be administered depending on the dosage and frequency as required and tolerated by the subject. A "patient" or "subject" for the purposes of the present invention includes both humans and other animals, particularly mammals. Thus the methods are applicable to both human therapy and veterinary applications. In the preferred embodiment the patient is a mammal, preferably a primate, and in the most preferred embodiment the patient is human. Other known therapies can be used in combination with the methods of the invention.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compositions of the present invention may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically or physiologically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intravenous, intramuscular, intraorgan, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

Preferred pharmaceutical preparations deliver one or more agents.

In use, the active agent utilized in the methods of the invention are administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, the effect sought, and the compound being employed. Determination of the proper dosage for a particular situation is within the skill of the practitioner.

EXAMPLES

The following examples are offered to illustrate aspects of, but not to limit, the claimed invention.

Example 1

Hepatocyte Transplantation (HT) Ameliorates Radiation-Induced Liver Damage (RILD) and Increases Survival after Partial Hepatic Resection and Irradiation (12)

Liver cancer is the sixth most common cancer worldwide in terms of number of cases (626,00/yr) but because of very poor prognosis, the number of deaths is almost the same as its incidence (598,000/yr). Besides primary liver cancer, metastatic liver cancer, arising from abdominal malignancies, remains a vexing and commonly encountered problem. Although, surgery is the only curative therapy, most patients with liver tumors are unresectable and chemotherapy fails to cure patients. This is rather unfortunate because a significant proportion of these patients have limited hepatic metastases (oligometastases), without harboring tumor deposits in extrahepatic sites. Failure to control the hepatic oligometastases results in eventual systemic progression of the cancer. In many cancers, such as head and neck, esophagus, lung, cervix and rectal cancer, radiation therapy (RT)± chemotherapy improves local tumor control and survival of patients. But RT has been traditionally used in a palliative role because of the potential for inducing potentially fatal RILD.

To simulate post-operative RT following resection of hepatic tumors, we examined RILD in F344 rats after HIR and partial hepatectomy (PH). HIR/RT induced severe RILD as evidenced by increased mortality and histopathological changes that included perivenous lobular collapse (FIG. 1A) with centrizonal steatosis (FIG. 1B), bile ductular proliferation and activation of liver stem cells, followed by periportal fibrosis (FIG. 1D-E). Since RT inhibited hepatic regeneration, we hypothesized that transplantation of unirradiated hepatocytes, via portal vein or intrasplenic injection, would result in preferential proliferation of the donor cells in the partially resected and irradiated host liver. Transplanted hepatocytes would further provide metabolic support and ameliorate consequences and mortality associated with RILD. We tested this hypothesis in F344 rats where dipeptidyl peptidase-positive (DPPIV+ve) F344 hepatocytes were transplanted into congeneic, DPPIV-ve F344 hosts after PH+HIR.

Figure 2:
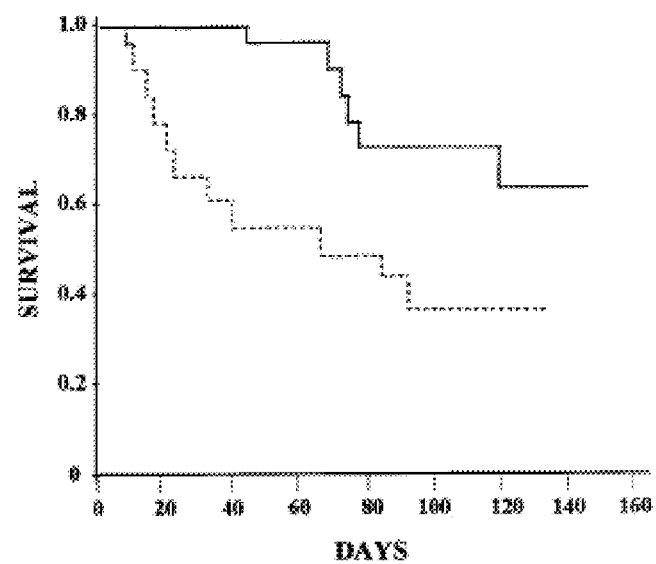
FIG. 2. HT Improves survival in rats that received PH+HIR. Kaplan-Meier analysis of survival shows improved survival (P=0.02, log-rank test) of PH+HIR-treated rats after HT versus PH+HIR alone.
Figure 3:
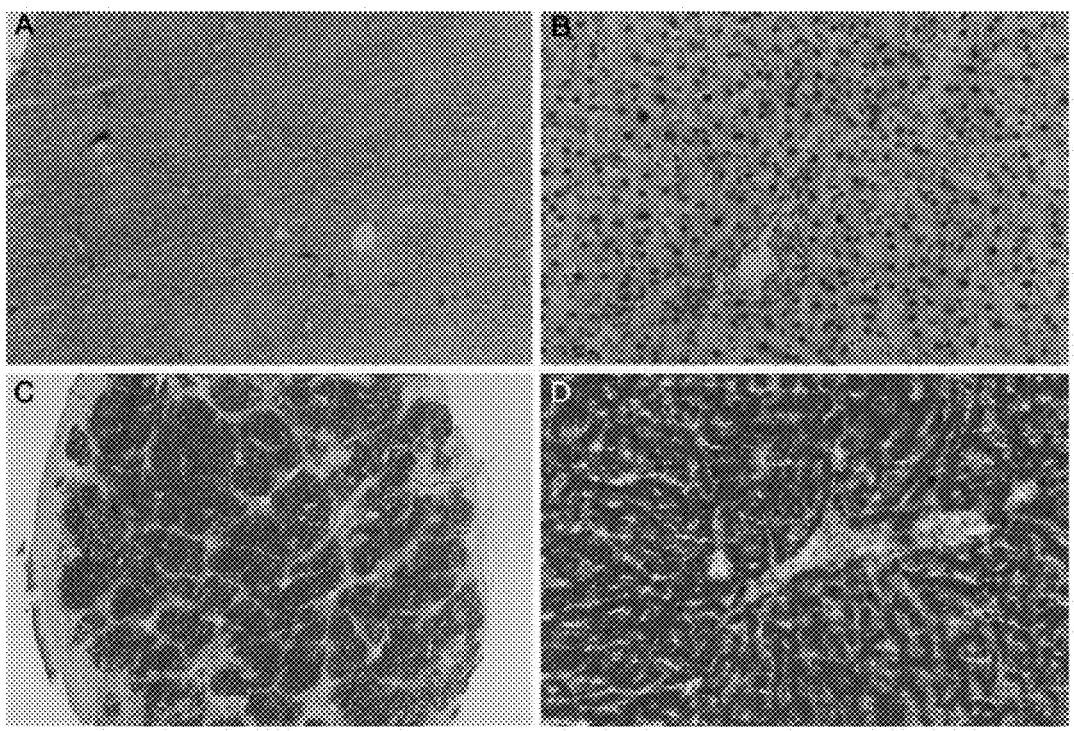
FIG. 3. DPPIV staining of livers. A (×4) and B (×320), PH+HT. C (×2) and D (×320), PH+HIR+HT. Note the near-total replacement of the irradiated host liver by DPPIV+ve transplanted cells (red stain) 12 weeks PH+HIR+HT.

We demonstrated that HT ameliorated the histological changes of RILD (FIG. 1 C, F) and increased survival of irradiated F344 rats (FIG. 2). By 12 weeks, donor hepatocytes constituted 76.9±3.9% of the host liver, in rats in the PH+HIR+HT group (FIG. 3C,D). In contrast, among the rats that received PH without HIR, the donor cells accounted for only 12.7±1.8% of the recipient liver hepatocytes after 12 weeks (p=0.006, t-test) (FIG. 3). This is the first demonstration of amelioration of RILD by HT and indicates one can rescue liver function with HT in patients having unresectable liver cancer after high dose chemo-RT.

Example 2

PH+HIR as a Preparative Regimen for Liver Repopulation by Transplanted Hepatocytes (Guha, C. et al., *Hepatology*, 36:354-362 (2002))

Figure 4:
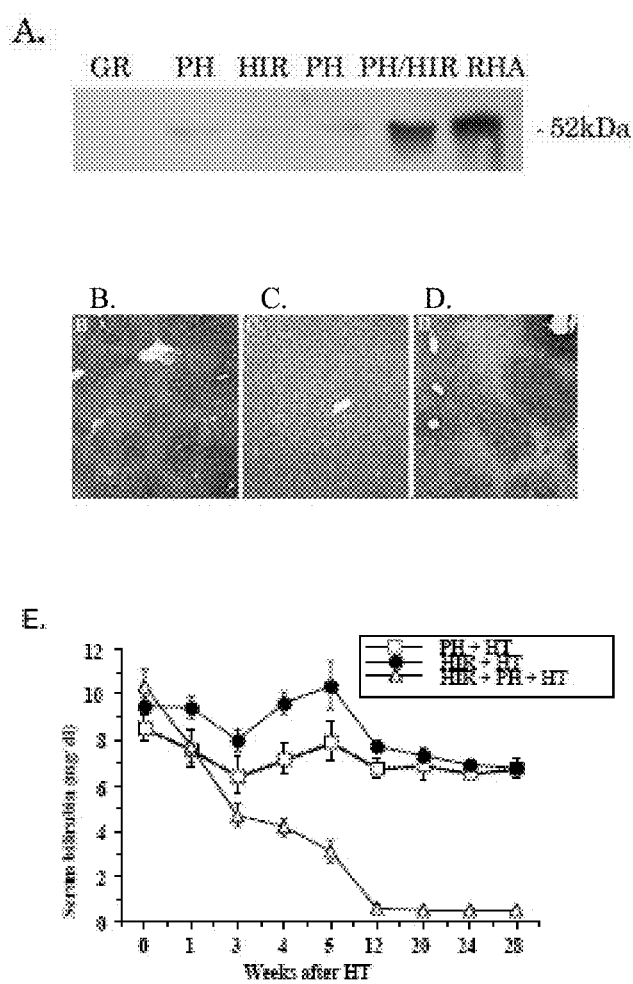
FIG. 4. Complete long-term normalization of serum bilirubin levels by extensive repopulation of Gunn rat (GR) liver by normal hepatocytes, transplanted after PH+HIR. Results shown are 5 months after HT in GR treated with PH+HIR. A. UGT1A1 immunoblot analysis of GR liver homogenates. Note the presence of UGT1A1 band in GR treated with PH+HIR. B-D. UGT1A1 immunohistochemical staining of liver sections-B, Wistar-RHA; C, GR; D, GR after PH+HIR+HT. E. Serum bilirubin levels after HT in Gunn rats receiving PH (n=4, □), HIR (n=4, ●), or HIR+PH (n=9, Δ).

Encouraged by our findings, we examined whether PH+HIR could be used as a preparative regimen of HT for amelioration of inherited metabolic liver diseases. Gunn rat is an animal model for bilirubin-uridinediphosphoglucuronate glucuronosyltransferase (UGT1A1) deficiency, which causes Crigler-Najjar syndrome type 1 in humans. UGT1A1 deficiency results in the lack of glucuronidation of bilirubin, resulting in the accumulation of unconjugated bilirubin in plasma and consequent bilirubin encephalopathy. We transplanted congeneic UGT1A1-proficient, Wistar-RHA hepatocytes in jaundiced Gunn rats, 4 days after PH+HIR. Five months after HT, there was 60-80% repopulation of the host liver by the engrafted UGT1A1+ve, transplanted hepatocytes (FIG. 4B-D). HPLC of bile collected 5 months after PH+HIR+HT showed complete normalization of the pigment profile, with excretion of conjugated bile pigments. There was complete normalization of serum bilirubin levels in the transplanted Gunn rats, which received PH+HIR+HT. In this group (n=9), serum bilirubin concentrations declined from initial levels of 10.4±2.3 mg/dl to completely normal levels (0.64±0.16 mg/dl) by 12 weeks (p=0.00012, t-test). In rats receiving either PH or HIR alone before HT, serum bilirubin concentrations declined by 25-30% in 28 weeks (FIG. 4E), indicating minimal repopulation. The complete normalization of serum bilirubin with PH+HIR has never been seen with current protocols of HT that are available in the clinic for Crigler-Najjar patients. These results indicate that HT in combination with a preparative regimen of HIR can be a highly effective treatment for such patients.

Example 3

Noninvasive Substitutes to PH in the Preparative Regimen of HT

The success of PH+HIR as a preparative regimen for HT depends on HIR suppressing the host hepatocellular proliferation and inducing mitotic catastrophe in host cells, while PH providing the mitotic stimuli and a selective growth advantage for transplanted hepatocytes. Although PH provides a very strong mitotic stimulus to the hepatocytes, it is invasive and is not desirable in clinical protocols of liver repopulation of transplanted hepatocytes for patients with metabolic disorders. We, therefore, examined noninvasive alternatives to PH (Table 2) (Takahashi, M. et al., *Gene Ther,* 10:304-313 (2003); Deb, N. et al., *Hepatology,* 34 (4):153A., 34:153A (2001); Parashar, B. et al., *Hepatology,* 32:206A (2000); Guha, C. et al., *Am J Nephrol,* 25:161-170 (2005); Malhi, H. et al., *Proc Natl Acad Sci USA,* 99:13114-13119 (2002)).

TABLE 2

HIR-BASED PREPARATIVE REGIMENS OF LIVER REPOPULATION (SUBSTITUTES TO PH)

| PREPARATIVE REGIMEN | MECHANISM OF REPOPULATION | EFFICACY |
|---|---|---|
| COMPENSATORY REGENERATIVE STIMULI | | |
| 1. HIR + Anti-Fas or FasL (Takahashi, M. et al., *Gene Ther,* 10: 304-313 (2003)) <br> 2. HIR + Portal vein branch ligation (Deb, N. et al., *Hepatology,* 34 (4): 153A., 34: 153A (2001)) <br> 3. HIR + Ischemia-reperfusion injury (Malhi, H. et al., *Proc Natl Acad Sci USA,* 99: 13114-13119 (2002)) | Fas-induced apoptosis in host cells <br> PVBL-induced apoptosis <br> Oxidative injury to host <br> HIR-induced injury to host cells <br> Compensatory regenerative stimuli | Extensive liver repopulation of transplanted hepatocytes. <br> Partial HIR results in selective repopulation in a single lobe of the liver. <br> Potential regimen for Cancer patients. |
| DIRECT HEPATIC MITOGENS | | |
| 4. HIR + Thyroid hormone (T3) (Parashar, B. et al., *Hepatology,* 32: 206A (2000)) <br> 5. HIR + Adeno-Hepatocyte Growth Factor (HGF) (Guha, C. et al., *Am J Nephrol,* 25: 161-170 (2005)) | HIR-induced genotoxic injury to host <br> Hepatic mitogen provides selective growth advantage to transplanted cells | Extensive repopulation. <br> Partial HIR results in single lobe repopulation. <br> Potential regimen for patients with metabolic disorders. |

Our results demonstrate that HIR in combination with a variety of mitotic stimuli (Table 2) can stimulate preferential proliferation of transplanted hepatocytes in rat and mouse livers. These experiments demonstrated that HIR induces genotoxic injury to the host hepatocytes, resulting in cell cycle arrest, accelerated senescence and mitotic catastrophe, in response to a mitotic stimulus, such as PH or HGF. In contrast to the host hepatocytes, the nonirradiated transplanted hepatocytes preferentially proliferated in response to the same mitotic stimulus. The gradual loss of host hepatocytes over a period of 3-5 months decreases the risk of sudden liver failure and provides regenerative stimuli to the transplanted cells over a long period of time. This also gave the engrafted cells time to proliferate and provide metabolic support to the diseased liver.

PH, PVBL and Fas-based strategies can provide compensatory regenerative stimuli to donor cells, while the host cells are prevented from dividing by HIR. These methods can find use in patients with liver cancer where the tumor with adjacent host liver tissue can be resected or ablated followed by HIR and transplantation of autologous hepatocytes after purging tumor cells (analogous with bone marrow rescue). The second method can use direct hepatic mitogens, such as, T3 and HGF. Accordingly, these protocols can be applied in patients with inherited or other liver diseases. Additionally, as shown in Table 2, a variety of proliferative stimuli can be used in combination with HIR to promote extensive liver repopulation by the transplanted cells.

Example 4

Focal Liver Irradiation for Selective Lobar Repopulation

Figure 5:
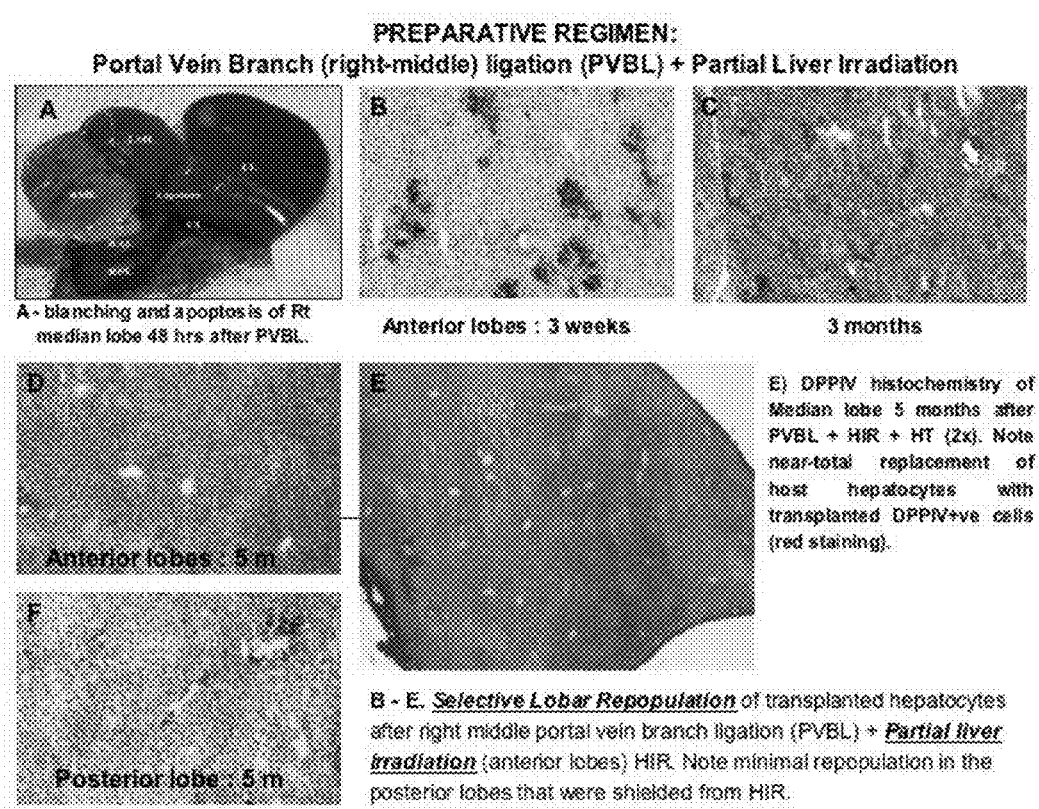
FIG. 5. Extensive liver repopulation by DPPIV+ve hepatocytes) in livers of DPPIV-ve F344, congeneic rats, that were subjected to HIR+PVBL. Selective ligation of the portal venous branch results in their atrophy and induction of regeneration in the residual lobes. The right branch of the portal vein was ligated, followed by irradiation of the anterior liver lobes after blocking the right posterior and the caudate lobes in DPPIV-ve F344 rats. Note selective repopulation of the anterior lobes (median and right anterior) by the transplanted cells in these animals (B-E, Anterior lobe; F, Caudate lobe). A, blanching and apoptosis of right median lobe 48 hours after PVBL. B. Anterior lobes at 3 weeks. C. Anterior lobes at 3 months. D. Anterior lobes 5 months. E. DPPIV histochemistry of median lobe 5 months after PVBL+HR+HT (2×). Note the near total replacement of the host hepatocytes with transplanted DPPIV+ve cells. B to E. Selective lobar repopulation of transplanted hepatocytes after right middle vein branch ligation (PVBL)+partial liver irradiation (anterior lobes) HIR. Note minimal repopulation in the posterior lobes that were shielded from HIR. F. Posterior Lobe 5 months.
Figure 6:
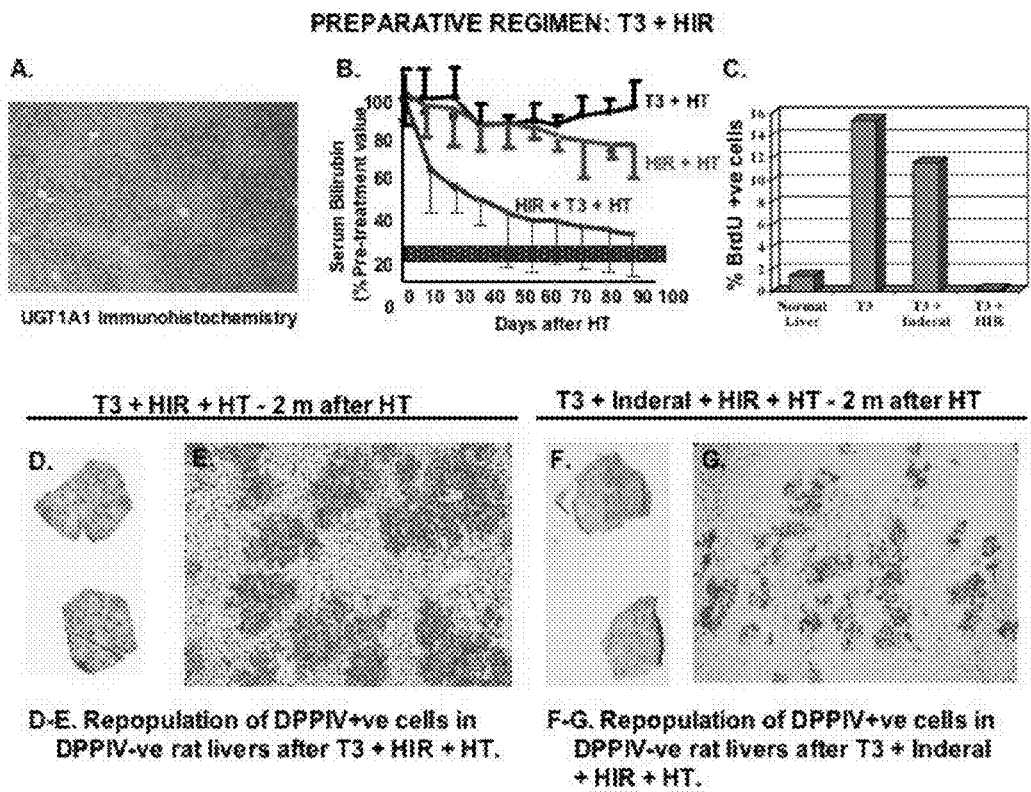
FIG. 6. Preparative regimen of HIR (50 Gy)+Tri-iodothyronine (T3) (400 μg/day subQ, every 10 days after HT). A, Extensive repopulation in Gunn rats. B, Normalization of serum bilirubin in Gunn rats after HIR+T3+HT. Note that HT after HIR or T3 alone fails to normalize the serum bilirubin. C, T3 induces DNA synthesis in liver cells, which is not suppressed by inderal. D-E, Extensive liver repopulation after T3+HIR. F-G, Moderate liver repopulation after T3+Inderal+HIR. This regimen could be clinically useful, as it allows hepatocyte repopulation without the cardiac side effects of tachycardia produced by T3.
Figure 7:
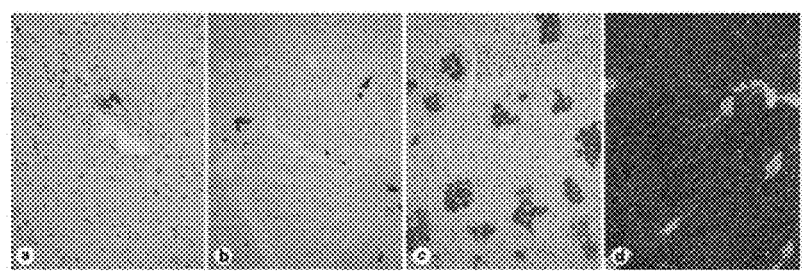
FIG. 7. HT following HIR and systemic administration of recombinant adenovirus expressing human Hepatocyte Growth (HGF). Beta-Gal+ve Rosa hepatocytes were transplanted in congeneic C57Bl/6 mice that received HIR (50 Gy)+Adeno-HGF injection. Histochemical staining of frozen liver sections for beta-galactosidase 2 (a), 4 (b), 8 (c) and 20 (d) weeks after HT.
Figure 8A:
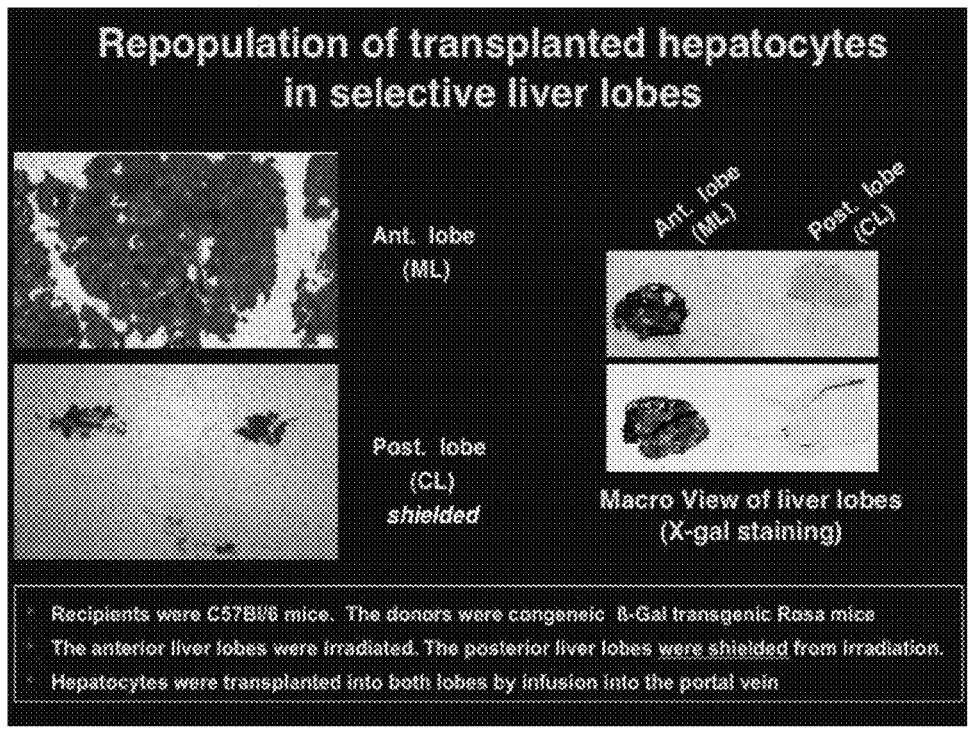
FIGS. 8A and 8B. Focal HIR promotes selective lobar repopulation. Repopulation of beta-gal+ve Rosa transplanted hepatocytes in irradiated anterior lobe as compared to shielded posterior lobe. 8B. A single liver lobe or a portion of the Right anterior lobe in C57Bl/6 mice after a regimen of regional/focal HIR+Ad-HGF.
Figure 8B:
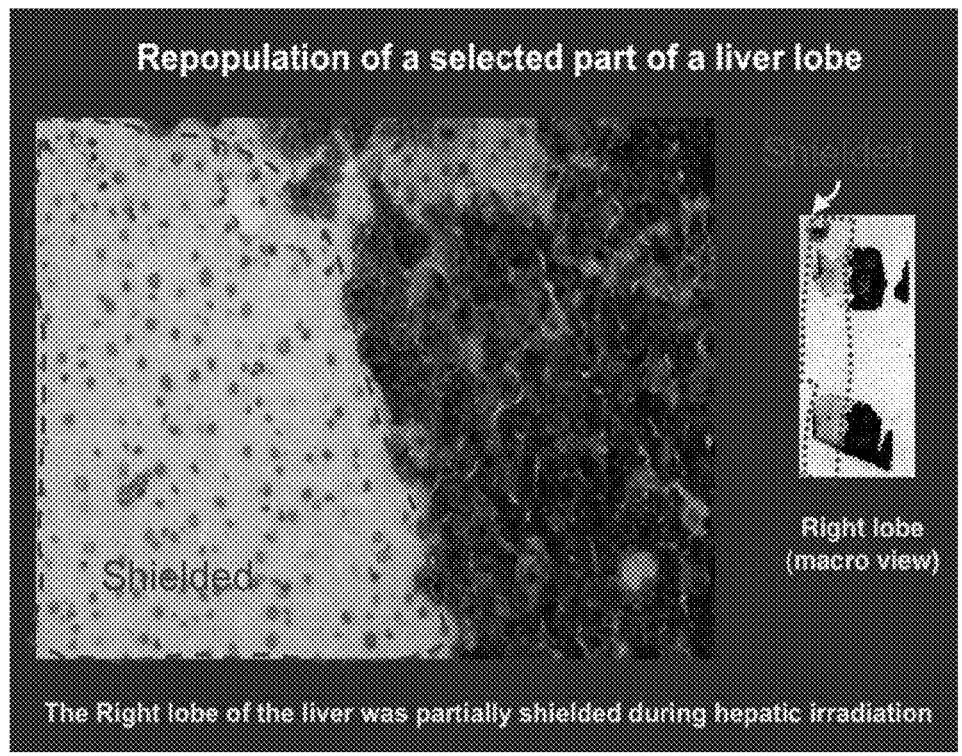

Irradiation to a portion of the whole liver is well tolerated in cancer patients. Doses higher than 50 Gy to parts of the liver can safely be offered to patients in the clinic with modern techniques of 3-D conformal RT or intensity-modulated RT. This is because clinical hepatic injury induced by irradiation is a function of dose and the volume of liver that is irradiated. Clinical trials have demonstrated that RILD or liver failure is not precipitated even when one-third of the liver receives a RT dose of 70-80 Gy (Dawson, L. et al., *Int J Radiat Oncol Biol Phys,* 53:810-821 (2002); Dawson, L. et al., *Semin Radiat Oncol,* 11:240-246 (2001)). We hypothesized that administration of focal liver irradiation would provide selective growth advantage of the engrafted hepatocytes, only in irradiated lobes. This would enable us to repopulate a single lobe of the liver or a portion of a single lobe by delivering focal high dose HIR. To provide mitotic signals, a compensatory regenerative signal following right portal vein branch ligation (PVBL) was used (see, Deb, N. et al., *Hepatology,* 34 (4): 153A., 34:153A (2001)) (FIG. 5) and direct mitogens, Tri-iodo thyronine (T3) (FIG. 6), and HGF (FIG. 7). PVBL+ partial HIR experiments were performed in DPPIV model, while adeno-HGF+partial HIR was performed in the rosa/ C57Bl/6 model. As seen in FIG. 5 B-E, clusters of red DPPIV+ve hepatocytes appeared by 3 weeks. There was gradual repopulation of the anterior irradiated lobes with near-total replacement of the lobe by 5 months (FIG. 5 E). In contrast, the posterior lobes that did not receive HIR failed to be repopulated by the donor cells (FIG. 5 F). The ability of partial HIR to induce selective lobar repopulation was confirmed in the rosa model of HT, following administration of adeno-HGF and HIR (FIG. 8). C57Bl/6 mice received HIR (50 Gy) to the anterior liver lobes after shielding the caudate and the right posterior lobe, followed by an intravenous injection of a recombinant adenoviral vector expressing human HGF ($1 \times 10^{11}$ particles). Two days after HIR, they received a transplantation of 0.5-1.0 million congenic rosa hepatocytes, there was selective repopulation of the irradiated anterior lobes (FIG. 8). Results show that adeno-HGF+HIR enabled near-total repopulation of the host liver by beta-galactosidase-positive transgenic hepatocytes within 4 months of HT (FIG. 7-8). The ability to selectively repopulate portions of the liver is unique to HIR-based repopulation protocols. It is contemplated for most metabolic liver diseases, functional correction of a fraction of the liver mass (10-25%) would be sufficient for significant clinical benefit and cure. Thus, the use of focal HIR to selectively repopulate a portion of the liver can enhance the safety because the larger portion of the liver would not be subjected to irradiation.

Example 5

Ex Vivo UGT1A1 Gene Therapy for Gunn Rats Using Preparative Regimens of Massive Liver Repopulation with Genetically Modified Hepatocytes Having described a safe and reproducible method of massive hepatic repopulation, we wanted to evaluate whether the liver could be repopulated by hepatocytes that have been genetically modified ex vivo. We have used Gunn rat hepatocytes that had been conditionally immortalized by transduction with a thermolabile SV40 T antigen in our laboratory (Fox, I. et al., *Hepatology*, 21:837-846 (1995)). These hepatocytes proliferate at 33° C., but at physiological temperatures (37° C. to 39° C.), the T antigen is degraded, and the hepatocytes stop proliferating and exhibit liver-specific functions. The cells were further transduced using a retroviral vector expressing human UGT1A1 and several transduced colonies were cloned by serial dilution (Tada, K. et al., *Liver Transpl Surg*, 4:78-88 (1998)). We transplanted these UGT1A1-transduced conditionally immortalized Gunn rat hepatocytes into autologous Gunn rats after a preparative regimen of PH+HIR. FIG. 9A, shows the experimental design. Immunohistochemical staining using anti-UGT1A1 antibodies demonstrate progressive repopulation of the genetically engineered conditionally immortalized Gunn rat hepatocytes expressing the human UGT1A1 transgene (FIG. 9B). By 16 weeks, there was near total replacement of the irradiated host liver. The physiological functioning of the transplanted cells was evident by the gradual decrease in serum bilirubin with complete correction of hyperbilirubinemia and jaundice by 12 weeks (FIG. 9C).

Example 6

Treatment of a Human with Chronic Liver Disease

Treatment of a human with metabolic or chronic liver failure as revealed by abnormal liver function tests is first treated with a dose of x-ray radiation 10 to 30 Gy to one or more lobes of the liver. The remainder of the exposed subject and liver is shielded from the radiation. Subsequently, $5 \times 10^{10}$ to $5 \times 10^{12}$ ex vivo hepatocytes (freshly harvested from a suitably matched human donor) per kg of body weight are administered to the patient and the patient is started on a daily regimen of recombinant human hepatocyte growth factor continuous infusion over 1 to 3 days, repeated over several weeks and recombinant epidermal growth factor (1 mg/kg) for two months and immunosuppressive therapy. The irradiated portion of the liver is biopsied at 2, 4, and 8 weeks and engrafted hepatocytes are identified by distinguishing cells according to a difference in their genomic nucleic acid sequence. Liver function tests are performed weekly to assess liver function. Over the period of monitoring the number of engrafted cells as a percent of the biopsied cells reaches 50% and the liver function tests return to more normal values.

Example 7

In this report, we report on the differentiation of oval cells into adult hepatocytes and bile ducts upon transplantation into liver that has been treated with a preparative regimen of hepatic irradiation (HIR) and systemic injection with adenovirus expressing human hepatocyte growth factor (Ad-HGF). We report that adult hepatic progenitor cells can engraft, integrate and proliferate in irradiated rat livers that have also received adeno-HGF.

Summary of Liver Stem Cell Transplantation Experiments.

Although adult hepatic progenitor/stem cells (HPC) are normally not seen in the liver, they expand and regenerate an injured liver when primary hepatocytes fail to proliferate. The role of HPC in the repair of radiation-induced liver damage (RILD) is unknown. The question whether HPCs would proliferate and compensate for parenchymal cell loss in a rodent model of RILD, induced by partial hepatectomy (PH) and hepatic irradiation (HIR) was investigated in this example by examining whether HPC proliferation is associated with liver regeneration after PH+HIR in F344 rats. Furthermore, the questions whether HPCs engraft and preferentially proliferate and repopulate in an irradiated rat liver following HIR and administration of a hepatic mitotic stimulus, such as, PH or administration of hepatocyte growth factor (HGF), was investigated.

In these experiments, dipeptidyl peptidase IV (DPPIV)-deficient (DPPIV-ve) F344 rats received PH, followed by HIR (50Gy) to the anterior liver lobes after exposing the liver by laparotomy and shielding the posterior liver lobes and other abdominal organs. Separate cohorts received HIR followed by an injection of a recombinant adenoviral vector expressing human HGF (Ad-HGF, $1 \times 10^{11}$ particles). One day after HIR, $1 \times 10^7$ freshly isolated, DPPIV-positive (DPPIV+ve) HPCs were transplanted into the liver of the DPPIV-ve rats by intrasplenic injection. HPCs were isolated from congeneic DPPIV+ve F344 rats that were previously treated either with D-galactosamine or with 2-acetylaminofluorence and PH to induce hepatic injury. Since HPCs are smaller in size than adult primary hepatocytes, HPCs were purified from the liver nonparenchymal cell fraction by discontinuous Nycodenz gradients or by using epithelial cell adhesion molecule (EpCAM)-coated magnetic beads for positive selection. Animals were sacrificed at 2, 6 and 8 weeks after treatment. Proliferation of HPCs and liver repopulation were detected by OV-6 immunohistochemistry and DPPIV histochemical staining.

With respect to activation and proliferation of oval cells in PH+HIR-treated animals. H&E staining of frozen liver sections revealed that the OV-6+ve HPC cells were activated and proliferated between 2-6 weeks after PH+HIR, indicating that HPC population participates in liver regeneration following HIR. Typically, oval cells appeared as small size, with an oval nucleus and scanty cytoplasm and were predominantly present at the interface between the portal tracts and the hepatic parenchyma. They formed tubular structures with poorly defined lumen and no basement membrane and were Immunoreactive for CK19, OV6 and EpCAM. The distinct morphology and markers of oval cells were similar to those described in humans and rodents.

Figure 10:
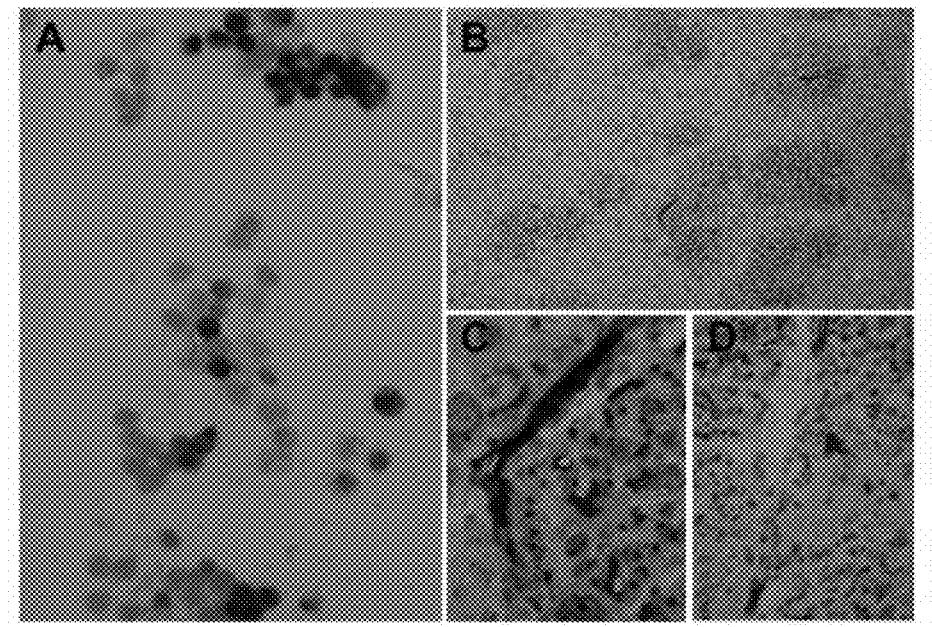
FIG. 10. Transplanted liver stem cells (oval cells, OC) differentiate into hepatocytes and bile ducts in rat livers treated with HIR and Ad-HGF. A: y-GGT staining on isolated oval cells before transplantation, B-D: DPPIV histochemistry of fresh frozen liver sections of F344 rats treated with HIR and Ad-HGF, 6 weeks after oval cell transplantation. C, DPPIV+ve bile duct. B and D, DPPIV+ve hepatocytes.
Figure 11:
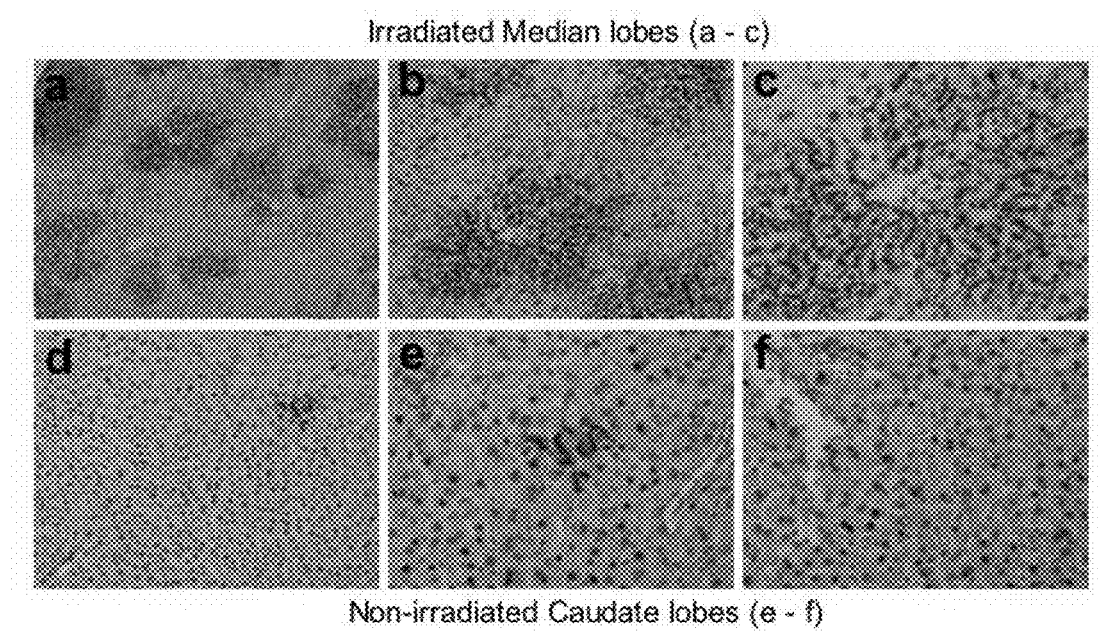
FIG. 11. Liver stem cells (oval cells, OC) proliferate and repopulate irradiated median lobes of rats treated with partial HIR (median lobe) and Ad-HGF. a-c, Liver repopulation in irradiated median lobes; d-f, engraftment of oval cells without liver repopulation in caudate lobes that were shielded and not irradiated. Note cell-cell competition between non-irradiated OC and irradiated host hepatocytes.

Hepatic oval cells were found to differentiate into hepatocytes and bile ducts in irradiated liver. To determine the repopulation potential of liver stem cells/HPC/oval cells in vivo, we isolated the oval cell-enriched non-parenchymal cells from rat livers treated with D-gal and 2-AAF, using the method of discontinuous Nycodenz density gradient. The non-parenchymal cells at the interface of 13% and 17% Nycodenz layers were collected. The number of oval cells was estimated by histochemical staining for GGT and immunostaining for CK19 and 15-20% of GGT+/CK19+ oval cells was found at the fraction. To determine the repopulation capacity of the oval cells in vivo, $1 \times 10^7$ of freshly isolated oval enriched non-parenchymal cells were transplanted into the liver of the DPPIV deficient Fisher rats through intrasplenic injection. The transplanted DPPIV competent oval cells in the DPPIV deficient host liver can be easily traced by histochemical staining or immunostaining for DPPIV. The recipients were treated with HIR and Ad-HGF prior to cell transplantation. Six weeks after transplantation, the differentiation and repopulation of transplanted oval cells in the recipient liver was evaluated. A significant part of recipient liver, around 40%, was replaced by transplanted oval cells (FIGS. 10 and 11). The regenerated hepatocyte nodules showed typical linear bile canalicular staining pattern for DPPIV. Around the regenerated hepatocyte nodules, DPPIV positive duct structures were also observed (FIG. 10). CK19 staining co-localized with the diffusely stained DPPIV ducts. These data demonstrated that transplanted oval cells showed bipotential characteristic by differentiating into hepatic and biliary lineages in the irradiated recipient liver.

Figure 12:
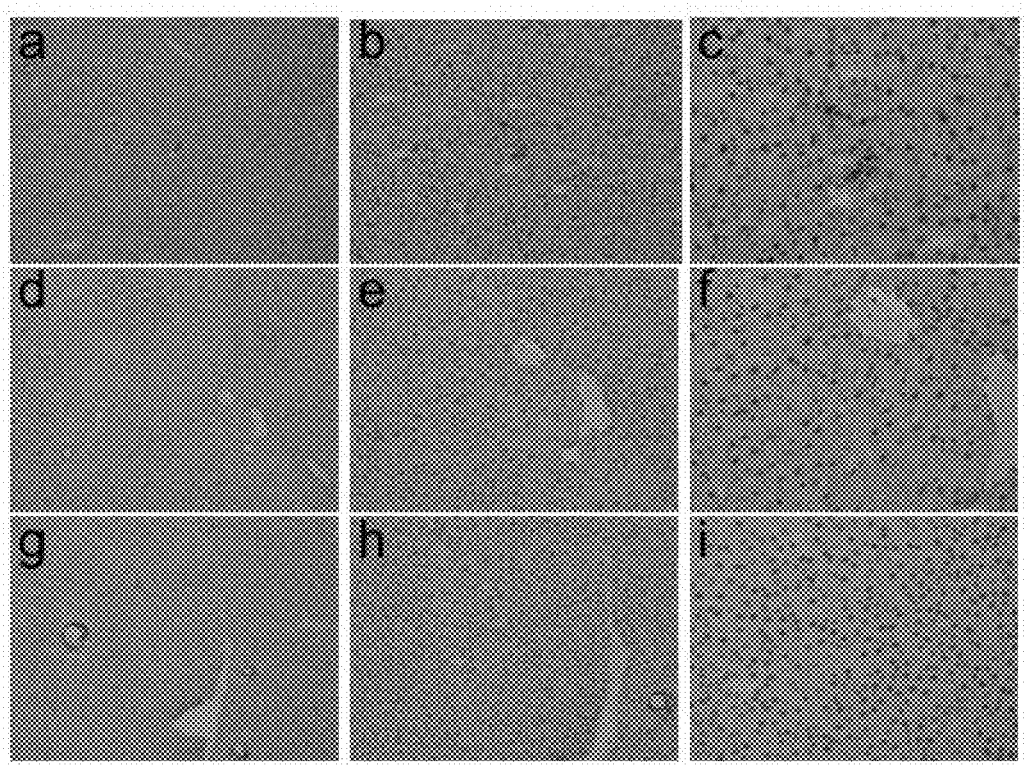
FIG. 12. Liver stem cells (oval cells) engraft but fail to proliferate in rats that received oval cell transplantation after treatment with either HIR alone (a-c) or Ad-HGF alone (d-f) or oval cell transplantation without any preparative regimen (g-i).

HGF was found to stimulate the proliferation and differentiation of transplanted oval cells in vivo. To define the condition of oval cell proliferation and differentiation in vivo, isolated oval cells were transplanted into the liver of normal DPPIV deficient rats and DPPIV deficient rats pretreated with Ad-HGF, HIR and HIR/Ad-HGF, respectively. Six weeks after cell transplantation, the repopulation of the liver was evaluated by histochemical staining for DPPIV activity. Compared to controls (Ad-HGF alone or HIR alone), livers of the rats subjected to HIR/Ad-HGF were significantly replaced by the DPPIV+hepatocytes after 6 weeks (p<0.01) (FIG. 11). However, transplantation of oval cells in normal rats, and rats subjected to HIR alone or Ad-HGF alone yields few scattered small DPPIV+hepatocyte clusters, which indicating no repopulation (FIG. 12).

Figure 13:
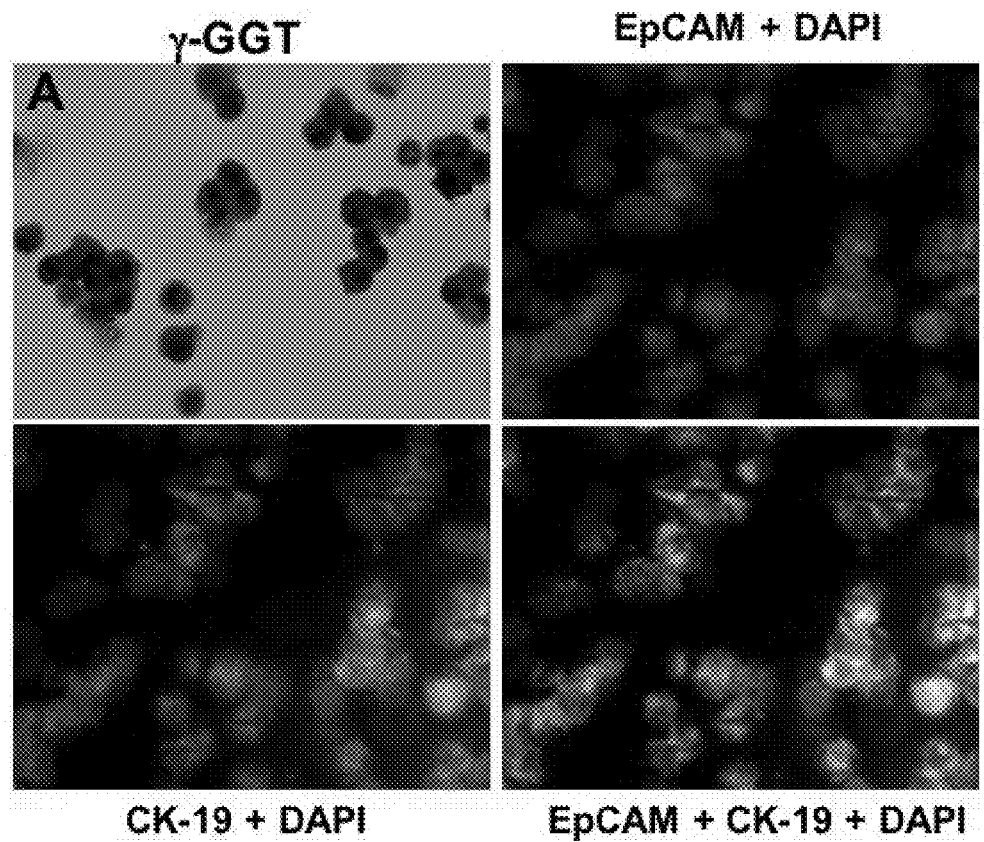
FIG. 13. Isolation of EpCAM+ve liver stem cells (oval cells) with magnetic beads. Immunocytochemistry with EpCAM and CK19.
Figure 14:
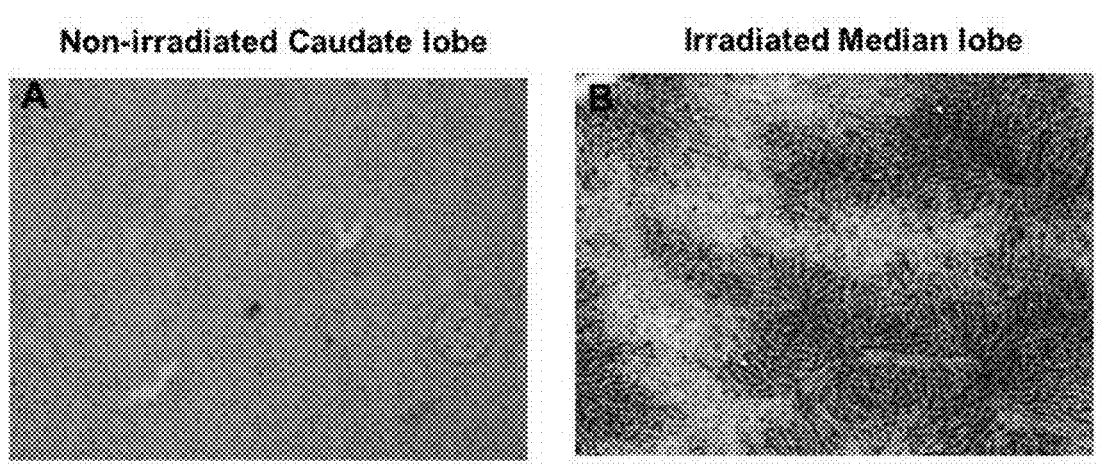
FIGS. 14A and 14B. EpCAM+ve liver stem cells proliferate and repopulate irradiated median lobes of rats treated with partial HIR (median lobe) and Ad-HGF. DPP1V histochemistry demonstrating DPPIV+ve transplanted donor hepatocytes in DPPIV-ve host liver.

EpCAM+cells showed liver repopulation capacity in the irradiated host liver. EpCAM+HPCs were isolated from the oval cell enriched non-parenchyma fraction (13/17%) using magnetic beads positive selection (FIG. 13) and their repopulation potential was evaluated in DPPIV deficient rats pretreated with HIR/Ad-HGF. EpCAM+ cells were also demonstrated GGT+/CK19+ by histochemical staining for GGT and immunostaining. Eight weeks after transplantation, radiation damaged host liver was significantly replaced by DPPIV positive hepatocytes (FIG. 14). There was near-total replacement of irradiated hepatic parenchyma by transplanted HPCs within 6 weeks after transplantation. EpCAM+ve HPC fraction exhibited a 40-60% repopulation of irradiated liver lobes by 8 weeks. In contrast, there was engraftment and minimal repopulation of HPCs in rat livers that received AdHGF alone (p<0.01) or in liver lobes that were shielded from HIR. H&E staining demonstrated a normal liver architecture in livers that received HPC transplantation after HIR.

Figure 15:
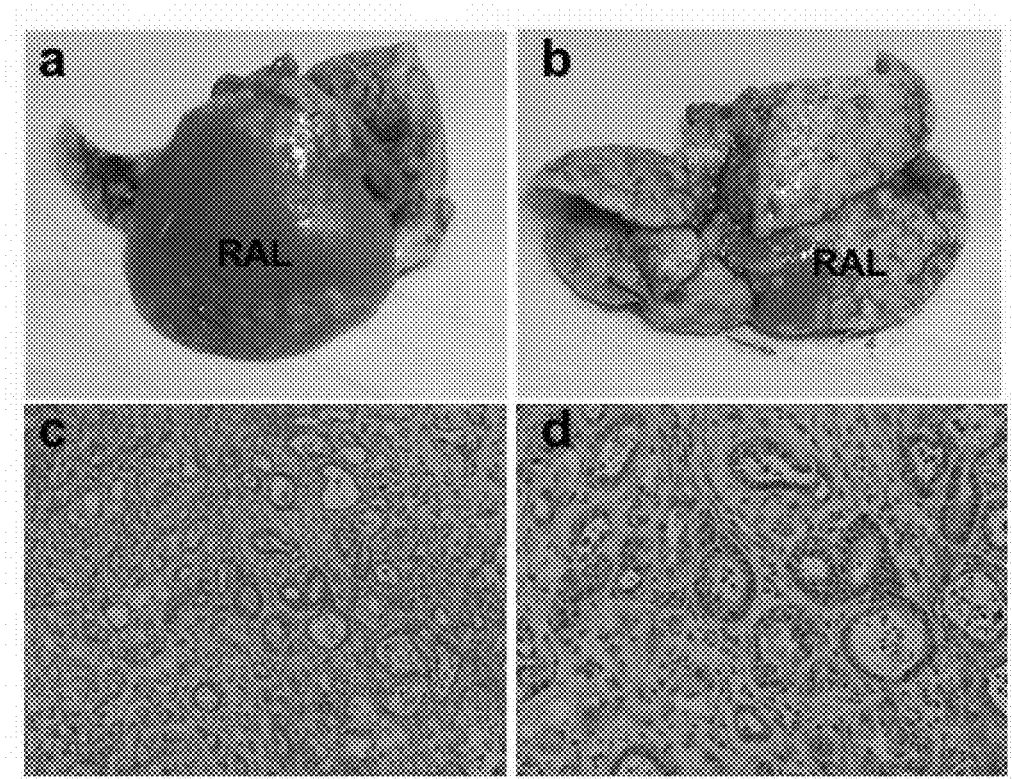
FIG. 15. Development of bile duct cancer after transplantation of liver stern cells (oval cells) in rats that received partial hepatectomy, Gross (a) anterior view, (b) posterior view of livers transplanted with liver cancer stem cells. (c), (d). Microscopic views of recipient liver after HE staining (c-10×, d-20×). RAL: right anterior lobe.
Figure 16:
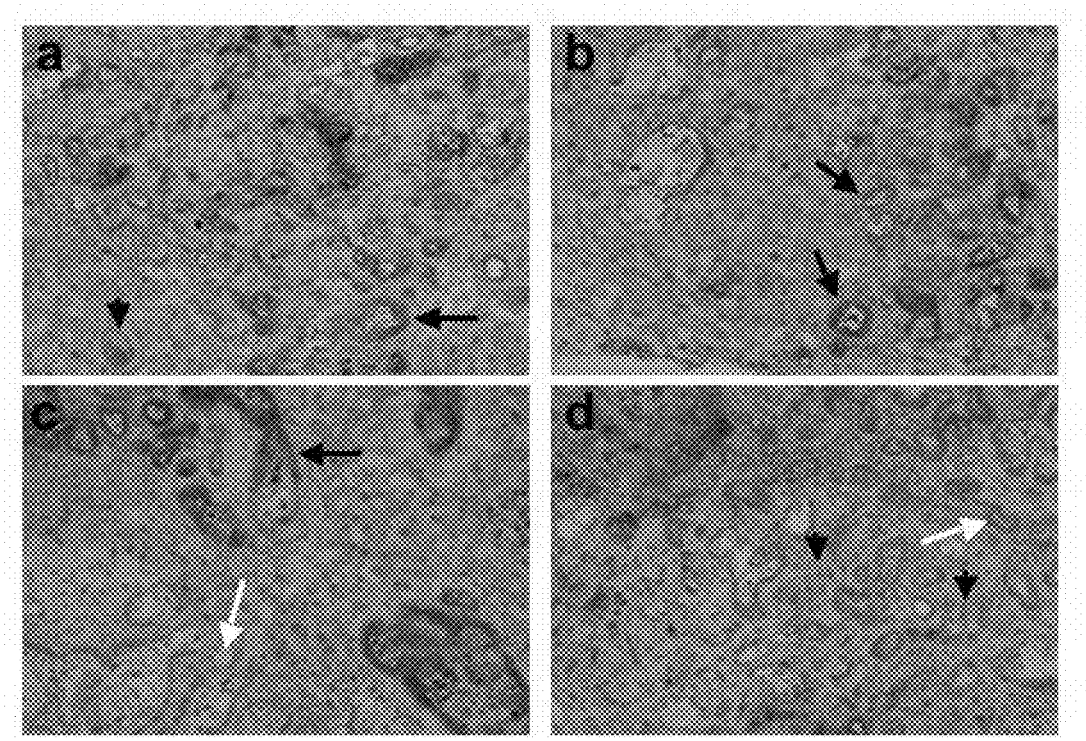
FIG. 16. Development of bile duct cancer after transplantation of liver stem (oval cells) in rats that received partial hepatectomy. DPP1V staining of recipient liver five weeks after partial hepatectomy and oval cell transplantation. Long arrows: strong DPPIV+ gland-like structure. Short black arrow: weak DPPPIV-gland-like structure. White arrow: DPPEV-gland-like structure.

Cholangiocarcinoma stem cells can be derived from oval cells and grown in rat livers. Oval cells are bipotential and are postulated to originate both hepatocellular or bile duct cancer. Oval cells that were cultured in vitro were transplanted into rats that received partial hepatectomy. Mitotic stimuli from partial hepatectomy resulted in the development of cholangiocarcinoma or bile duct cancer (FIGS. 15 and 16). Thus these models can be used to grow cancer stem cells in rat livers treated with HIR/PH.

Accordingly, amplification of adult HPC population in a rodent model of RILD has now been demonstrated. Adult HPC transplantation, combined with a hepatic mitotic stimulus, can engraft and rapidly regenerate liver tissues following high doses of HIR. EpCAM+ve HPCs had strong liver repopulation capacity. Accordingly, EpCAM is contemplated as a cell surface marker for HPCs which can be used to purify HPC population from donor livers. As HPCs exhibit bipotential differentiation towards both hepatocytic and biliary lineages, transplantation of HPCs can provide a salvage therapy for RILD and for the treatment of end-stage liver diseases.

The referenced patents, patent applications, and scientific literature, including accession numbers to GenBank database sequences, referred to herein are hereby incorporated by reference in their entirety. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

What is claimed is:

1. A method of treating a mammalian subject having a damaged central nervous system with a reduced function by engrafting mammalian ex vivo cells at the site of injury, the method comprising the steps of:
   (a) administering to the subject an effective amount of an agent that confers a growth disadvantage to at least a subset of endogenous nerve cells at the site of engraftment, wherein the agent is radiation;
   (b) administering to the subject an effective amount of a mitogenic stimuli for the ex vivo cells; and
   (c) administering the ex vivo cells to the subject, wherein the ex vivo cells engraft at the site of injury and repopulate at least a portion of the site with the ex vivo cells, wherein the repopulated ex vivo cells supplement the function and replace at least a subset of endogenous nerve cells,
   thereby treating the subject.

2. The method of claim 1, wherein the ex vivo cells are selected from the group consisting of adult somatic cells, adult neuron progenitor cells, adult stem cells, embryonic progenitor cells, fetal cells, xenogenic cells, and embryonic stem cells which are capable of populating the site of injury with neurons.

3. The method of claim 1, wherein administering to the subject an effective amount of radiation increases the engraftment of ex vivo cells at the site of injury.

4. The method of claim 1, wherein the radiation is Stereotactic Radiosurgery (SRS), Intensity-Modulated Radiation Therapy (IMRT), dynamic adaptive radiation therapy, image-guided radiation therapy (IGRT), spatially confined, focally ablative radiation, single-fraction irradiation, or hypofractionated irradiation.

* * * * *